(12) United States Patent
Lee et al.

(10) Patent No.: US 8,697,658 B2
(45) Date of Patent: Apr. 15, 2014

(54) GLYCOSIDE COMPOUNDS

(71) Applicant: National Health Research Institutes, Miaoli County (TW)

(72) Inventors: Jinq-Chyi Lee, Miaoli County (TW); Yu-Sheng Chao, New York, NY (US)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 13/713,583

(22) Filed: Dec. 13, 2012

(65) Prior Publication Data
US 2013/0157970 A1 Jun. 20, 2013

Related U.S. Application Data

(60) Provisional application No. 61/576,102, filed on Dec. 15, 2011.

(51) Int. Cl.
| | |
|---|---|
| *A61K 31/70* | (2006.01) |
| *C07H 5/04* | (2006.01) |
| *C07H 5/06* | (2006.01) |
| *C07H 19/044* | (2006.01) |
| *C07H 7/06* | (2006.01) |

(52) U.S. Cl.
USPC ............ 514/23; 536/28.6; 536/29.2; 536/54; 536/55; 514/43

(58) Field of Classification Search
None
See application file for complete search history.

(56) References Cited

U.S. PATENT DOCUMENTS

| | | | | |
|---|---|---|---|---|
| 7,419,959 B2 * | 9/2008 | Eckhardt et al. | ................ | 514/23 |
| 7,662,790 B2 * | 2/2010 | Himmelsbach et al. | ........ | 514/23 |
| 7,776,830 B2 * | 8/2010 | Eckhardt et al. | ................ | 514/23 |
| 7,838,499 B2 * | 11/2010 | Chen et al. | ....................... | 514/23 |
| 7,851,617 B2 * | 12/2010 | Nomura et al. | ............... | 536/28.6 |
| 7,928,080 B2 * | 4/2011 | Townsend et al. | ............... | 514/43 |
| 7,935,674 B2 * | 5/2011 | Nomura et al. | .................. | 514/43 |
| 8,039,441 B2 * | 10/2011 | Himmelsbach et al. | ........ | 514/23 |
| 2006/0009400 A1 | 1/2006 | Eckhardt et al. | | |
| 2008/0139484 A1 | 6/2008 | Teranishi et al. | | |
| 2009/0074738 A1 | 3/2009 | Yonekubo et al. | | |

FOREIGN PATENT DOCUMENTS

| | | |
|---|---|---|
| JP | 2009-196984 | 9/2009 |
| WO | WO 2005/012326 | 2/2005 |
| WO | WO 2006/080577 | 8/2006 |
| WO | WO 2008/002824 | 1/2008 |
| WO | WO 2008/013322 | 1/2008 |
| WO | WO 2010/031820 | 3/2010 |
| WO | WO 2011/048148 | 4/2011 |
| WO | WO 2011/070592 | 6/2011 |

OTHER PUBLICATIONS

Adachi et al., Metabolism, vol. 49, No. 8, 2000, 990-995.*

* cited by examiner

*Primary Examiner* — Traviss C McIntosh, III
(74) *Attorney, Agent, or Firm* — Cesari and McKenna, LLP

(57) ABSTRACT

Compounds of formula (I):

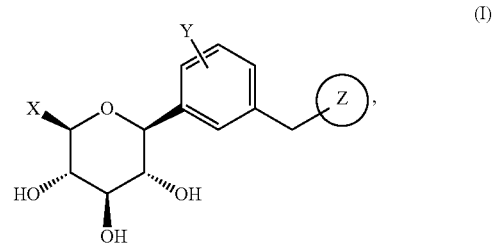

wherein X, Y, and Z are defined herein. Also disclosed are pharmaceutical compositions and therapeutical methods related to these compounds.

19 Claims, No Drawings

GLYCOSIDE COMPOUNDS

CROSS REFERENCE TO RELATED APPLICATIONS

This application claims priority to U.S. Provisional Application No. 61/576,102, filed on Dec. 15, 2011, the contents of which are hereby incorporated by reference.

BACKGROUND

Sodium-dependent glucose cotransporters ("SGLTs") are a family of glucose transporters.

Research shows that more than 99% of renal glucose is resorbed by two subtypes of SGLTs, i.e. SGLT1 and SGLT2. More specifically, about 10% of renal glucose reabsorption is accomplished by low-capacity, high affinity SGLT1, which is mainly expressed in the small intestine and the S3 segment of the kidney's proximal tubule; and about 90% of renal glucose reabsorption is mediated by high-capacity, low affinity SGLT2, which is found in the S1 segment of the kidney's proximal tubule. Inhibiting SGLT2 activities results in suppression of renal glucose reabsorption, thereby decreasing blood sugar level.

A number of SGLT2 inhibitors have been discovered. They have potentials to be used as anti-diabetic drugs. See e.g., Han et al., Diabetes, 2008, 57, 1723. Safe and efficacious drug candidates remain to be identified from SGLT2 inhibitors, both synthesized and not yet synthesized.

SUMMARY

This invention is based on the discovery that certain glycoside compounds are effective in treating SGLT2 mediated disorders.

In one aspect, this invention features glycoside compounds of formula (I):

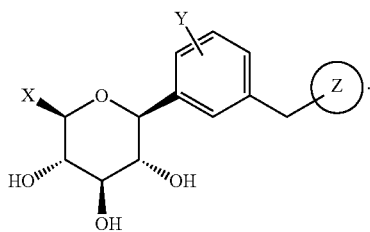

(I)

In this formula, X is $R_1ONHCH_2$—, $R_1R_2NNHCH_2$—, $R_1ON=CH$—, $R_1R_2NN=CH$—, $R_1HNC(S)NHCH_2$—, $R_1HNC(S)NHN=CH$—, or $R_1C(O)NHN=CH$—, in which each of $R_1$ and $R_2$, independently, is H, halo, $C_1$-$C_{10}$ alkyl, $C_1$-$C_{10}$ alkoxyl, $C_2$-$C_{10}$ alkenyl, $C_2$-$C_{10}$ alkynyl, $C_3$-$C_{10}$ cycloalkyl, $C_3$-$C_{10}$ heterocycloalkyl, aryl, or heteroaryl; Y is H, halo, amino, $C_1$-$C_{10}$ alkyl, or $C_1$-$C_{10}$ alkoxyl; Z is unsubstituted aryl or aryl substituted with halo, hydroxyl, amino, $C_1$-$C_{10}$ alkyl, $C_1$-$C_{10}$ alkoxyl, $C_3$-$C_{10}$ cycloalkyl, $C_3$-$C_{10}$ heterocycloalkyl, $C_2$-$C_{10}$ alkenyl, $C_2$-$C_{10}$ alkynyl, aryl, or heteroaryl.

One subset of the just-described compounds includes those in which Y is halo and Z is aryl substituted with $C_1$-$C_{10}$ alkoxyl or $C_3$-$C_{10}$ cycloalkyl.

In another aspect, this invention features glycoside compounds of formula (II):

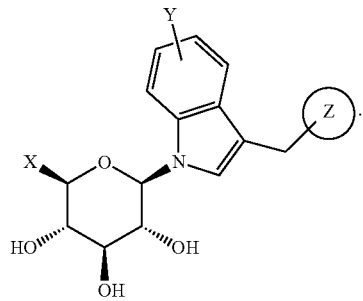

(II)

In formula (II), X is CN, heteroaryl, heteroaryl-$CH_2$—, $N_3CH_2$—, $NH_2CH_2$—, $R_1R_2NCH_2$—, $R_1C(O)NHCH_2$—, $R_1C(O)NHNHCH_2$—, $R_1HNC(O)NHCH_2$—, $R_1HNC(S)NHCH_2$—, $R_1ONHCH_2$—, $R_1R_2NNHCH_2$—, $R_{10}$—$N=CH$—, $R_1R_2NN=CH$—, or $R_1C(O)NHN=CH$—, in which each of $R_1$ and $R_2$, independently, is H, halo, $C_1$-$C_{10}$ alkyl, $C_1$-$C_{10}$ alkoxyl, $C_3$-$C_{10}$ cycloalkyl, $C_3$-$C_{10}$ heterocycloalkyl, $C_2$-$C_{10}$ alkenyl, $C_2$-$C_{10}$ alkynyl, aryl, or heteroaryl; or $R_1$ and $R_2$, together with the nitrogen atom to which they are attached, is heteroaryl; Y is H, halo, amino, $C_1$-$C_{10}$ alkyl, or $C_1$-$C_{10}$ alkoxyl; and Z is unsubstituted aryl or aryl substituted with halo, hydroxyl, amino, $C_1$-$C_{10}$ alkyl, $C_1$-$C_{10}$ alkoxyl, $C_3$-$C_{10}$ cycloalkyl, $C_3$-$C_{10}$ heterocycloalkyl, $C_2$-$C_{10}$ alkenyl, $C_2$-$C_{10}$ alkynyl, aryl, or heteroaryl.

One subset of the compounds described above includes those in which X is $R_1C(O)NHCH_2$— or $R_1C(O)NHNHCH_2$—, Y is H or halo, and Z is aryl substituted with $C_3$-$C_{10}$ cycloalkyl.

In still another project, this invention features glycoside compounds of formula (III):

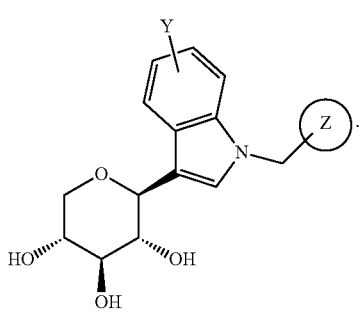

(III)

In this formula, Y H, halo, amino, $C_1$-$C_{10}$ alkyl, or $C_1$-$C_{10}$ alkoxyl; and Z is unsubstituted aryl or aryl substituted with halo, hydroxyl, amino, $C_1$-$C_{10}$ alkyl, $C_1$-$C_{10}$ alkoxyl, $C_3$-$C_{10}$ cycloalkyl, $C_3$-$C_{10}$ heterocycloalkyl, $C_2$-$C_{10}$ alkenyl, $C_2$-$C_{10}$ alkynyl, aryl, or heteroaryl.

One subset of the compounds of formula (III) includes those Y is H or halo, and Z is unsubstituted aryl or aryl substituted with $C_3$-$C_{10}$ cycloalkyl.

The term "alkyl" refers to a saturated, linear or branched hydrocarbon moiety containing 1-20 carbon atoms (e.g., $C_1$-$C_{10}$), such as —$CH_3$ or —$CH(CH_3)_2$. The term "alkenyl" refers to a linear or branched hydrocarbon moiety that contains at least one double bond and 2-20 carbon atoms (e.g., $C_2$-$C_{10}$), such as —CH=CH—$CH_3$. The term "alkynyl"

refers to a linear or branched hydrocarbon moiety that contains at least one triple bond and 2-20 carbon atoms (e.g., $C_2$-$C_{10}$), such as —C≡C—$CH_3$. The term "alkoxyl" refers to an —O-alkyl. Examples of alkoxyl include, but are not limited to, methoxy, ethoxy, n-propoxy, isopropoxy, n-butoxy, iso-butoxy, sec-butoxy, and tert-butoxy. The term "cycloalkyl" refers to a saturated, cyclic hydrocarbon ring system having 3-30 carbon atoms (e.g., $C_3$-$C_{10}$), such as cyclohexyl. The term "heterocycloalkyl" refers to a saturated, cyclic ring system having at least one heteroatom (e.g., N, O, or S), such as 4-tetrahydropyranyl. The term "aryl" refers to a 6-carbon membered monocyclic, 10-carbon membered bicyclic, 14-carbon tricyclic aromatic ring system. Examples of aryl moieties include phenyl (Ph), phenylene, naphthyl, naphthylene, pyrenyl, anthryl, and phenanthryl. The term "heteroaryl" refers to a 5-8 membered monocyclic, 8-12 membered bicyclic, or 11-14 membered tricyclic aromatic ring system having one or more heteroatoms (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, alkenyl, alkynyl, alkoxyl, cycloalkyl, heterocycloalkyl, aryl, and heteroaryl mentioned herein include both substituted and unsubstituted moieties, unless specified otherwise. Possible substituents on cycloalkyl, heterocycloalkyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, alkylimino, arylimino, $C_1$-$C_{10}$ alkylsulfonimino, arylsulfonimino, hydroxyl, halo, thiol, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

In another aspect, this invention features a method for treating a disorder related to SGLT2. The method includes administering to a subject in need thereof an effective amount of one or more glycoside compounds of formula (I)-(III) shown above. Examples of SGLT2 mediated disorders include diabetes mellitus (type 1 or type 2), diabetic retinopathy, diabetic neuropathy, diabetic nephropathy, insulin resistance, hyperglycemia, hyperinsulinemia, obesity, elevated blood levels of fatty acids, elevated blood levels of glycerol, hyperlipidemia, hypertriglyceridemia, Syndrome X, atherosclerosis, delayed would healing, or hypertension.

The method can further include administering to the subject an antidiabetic agent, an anti-obesity agent, an agent for treating diabetic complications, an antihypertensive agent, an antiplatelet agent, an anti-atherosclerotic agent, or a hypolipidemic agent.

Examples of an anti-diabetic agent include, but are not limited to, biguanides, thiazolidinediones, DPP-IV inhibitors, sulphonylureas, alpha-glucosidase inhibitors, incretin mimetics, mitiglinides, PPAR-gamma-agonists, PPAR-α/γ dual agonists, nateglinide, insulin and insulin analogues, PTP1B inhibitors, glycogen phosphorylase inhibitors, RXR modulators, glucose 6-phosphatase inhibitors, alpha2-antagonists, GLP-1 and GLP-1 analogues, amylin, and fructose 1,6-bisphosphatase inhibitors.

Examples of an anti-obesity agent include, but are not limited to, $β_3$ adrenergic agonists, anorectic agents, lipase inhibitors, serotonin (and dopamine) reuptake inhibitors, thyroid hormone beta drugs, NPY antagonists, Leptin analogues MC4 agonists and CB1 antagonists.

Examples of an agent for treating diabetic complications include, but are not limited to, protein tyrosine phosphatase-1B inhibitors, aldose reductase inhibitors, advanced glycation endproducts formation inhibitors, AGE breakers, sulodexide, 5-hydroxy-1-methylhydantoin, insulin-like growth factor-I, platelet-derived growth factor, platelet-derived growth factor analogues, epidermal growth factor, nerve growth factor, carnitine derivative, uridine, protein kinase C inhibitors, sodium channel antagonists, nuclear factor-kappaB inhibitors, Y-128, biomoclomol, lipid peroxidase inhibitors, N-acetylated-alpha-linked-acid-dipeptidase inhibitors, EGB-761, angiotensin-converting enzyme inhibitors and neutral endopeptidase inhibitors.

Examples of an anti-hypertensive agent include, but are not limited to, ACE inhibitors, calcium antagonists, alpha-blockers, diuretics, centrally acting agents, angiotensin-II antagonists, beta-blockers, rennin inhibitors, and vasopeptidase inhibitors.

Examples of an anti-platelet agent include, but are not limited to, abciximab, ticlopidine, eptifibatide, dipyridamole, aspirin, anagrelide, tirofiban and clopidogrel.

Examples of an anti-atherosclerotic agent include, but are not limited to, ACE inhibitors, beta-blockers, calcium antagonists, angiotensin-II antagonists, antiplatelets, anticoagulants, diuretics, statins, cholesterol absorption inhibitors, nicotinic acid and nicotinic acid derivatives, and bile acid sequestrants.

Examples of a hypolipidemic agent include, but are not limited to, MTP inhibitors, HMG CoA reductase inhibitors, squalene synthesase inhibitors, squalene epoxidase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, nicotinic acid and nicotinic acid derivatives, CETP inhibitors, and ABCA1 upregulators.

The term "treating" or "treatment" refers to administering one or more glycoside compounds to a subject, who has an above-described disorder, a symptom of such a disorder, or a predisposition toward such a disorder, with the purpose to confer a therapeutic effect, e.g., to cure, relieve, alter, affect, or ameliorate the above-described disorder, the symptom of it, or the predisposition toward it.

The glycoside compounds described above include the compounds themselves, as well as their salts, prodrugs, and solvates, if applicable. A salt, for example, can be formed between an anion and a positively charged group (e.g., amino) on a glycoside compound. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group (e.g., carboxylate) on a glycoside compound. Suitable cations include sodium ion, potassium ion, magnesium ion, calcium ion, and an ammonium cation such as tetramethylammonium ion. The glycoside compounds also include those salts containing quaternary nitrogen atoms. Examples of prodrugs include esters and other pharmaceutically acceptable derivatives, which, upon administration to a subject, are capable of providing active glycoside compounds. A solvate refers to a complex formed between an active glycoside compound and a pharmaceutically acceptable solvent. Examples of pharmaceutically acceptable solvents include water, ethanol, isopropanol, ethyl acetate, acetic acid, and ethanolamine.

Also within the scope of this invention is a pharmaceutical composition containing one or more of the glycoside compounds described above for use in treating one of the above-described disorders, and the use of such a composition for the manufacture of a medicament for this treatment.

The details of one or more embodiments of the invention are set forth in the description below. Other features, objects, and advantages of the invention will be apparent from the description and from the claims.

DETAILED DESCRIPTION

Shown below are exemplary compounds of this invention:

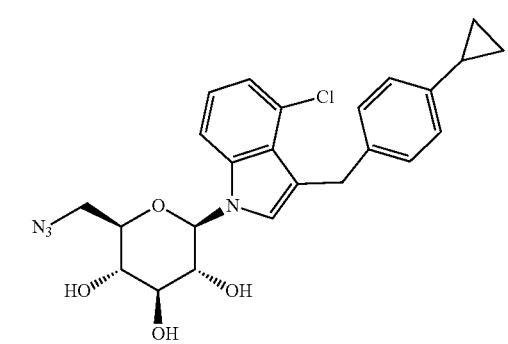

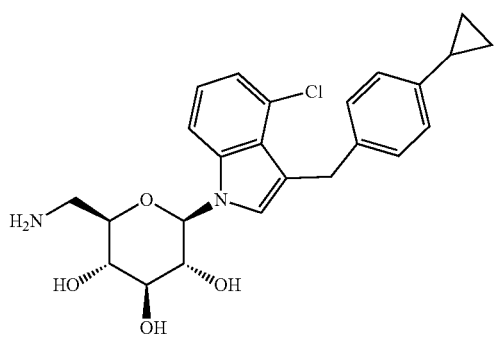

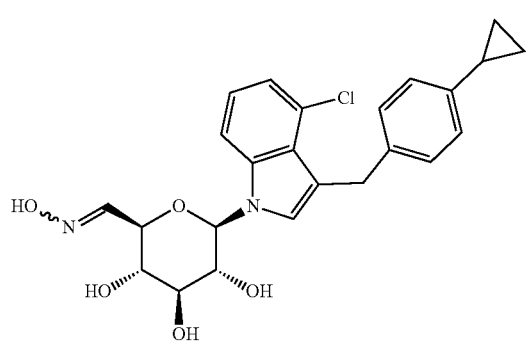

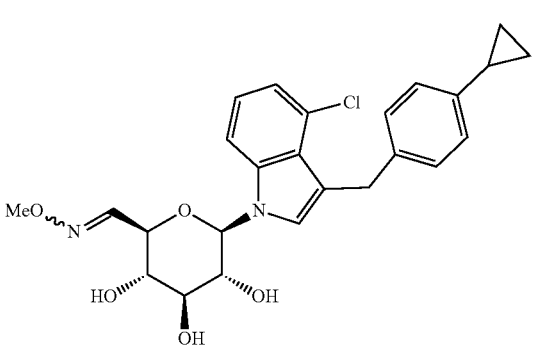

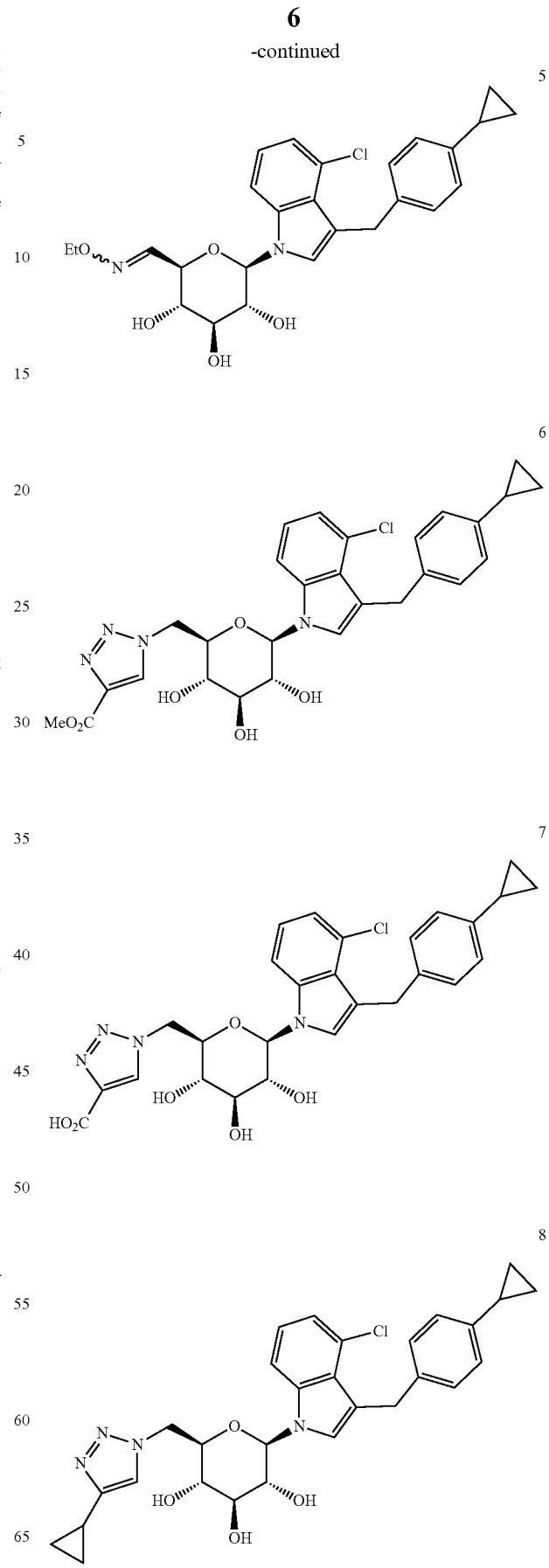

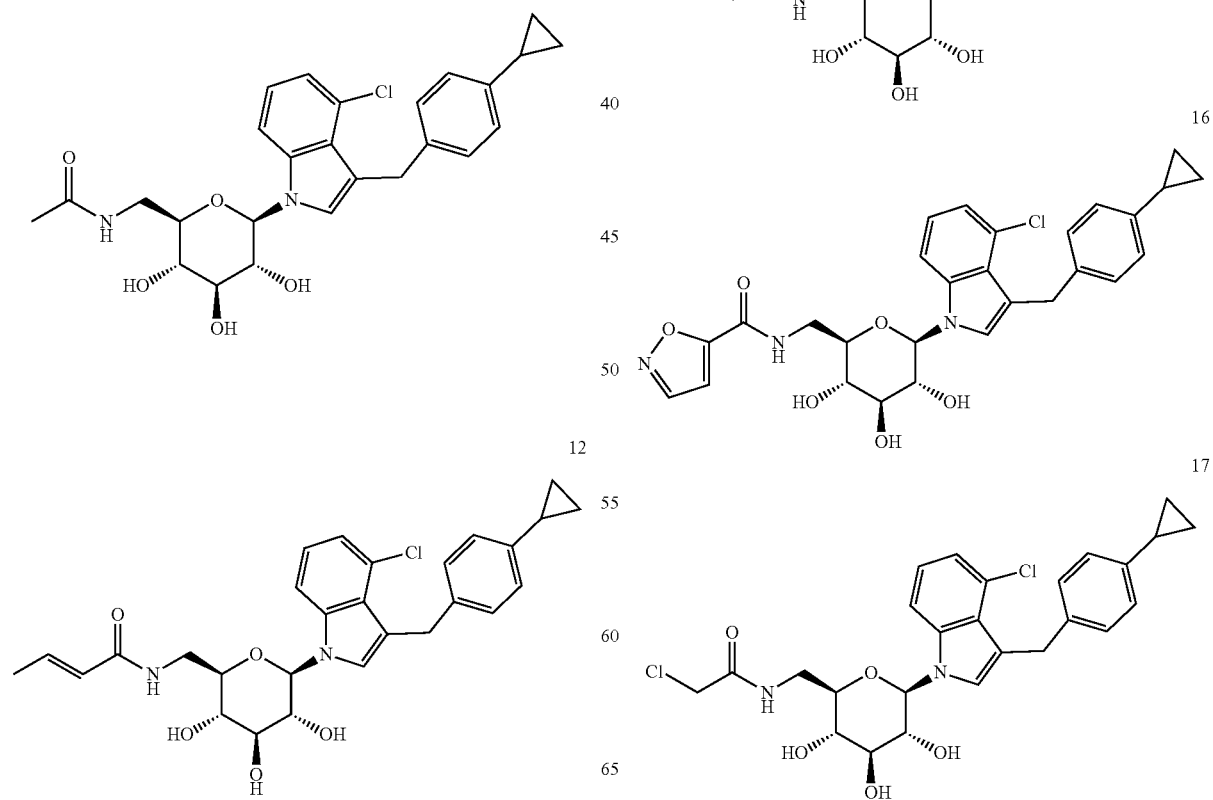

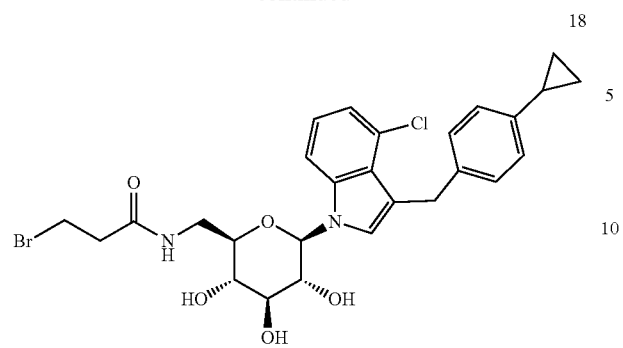
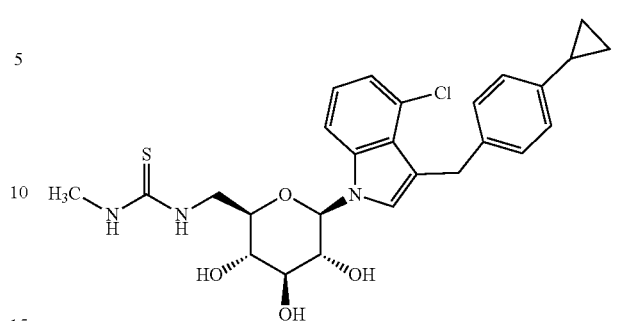
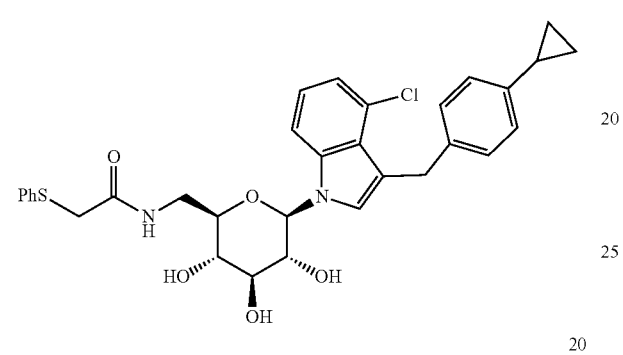
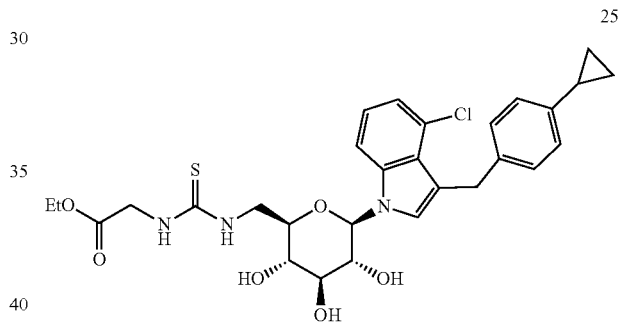
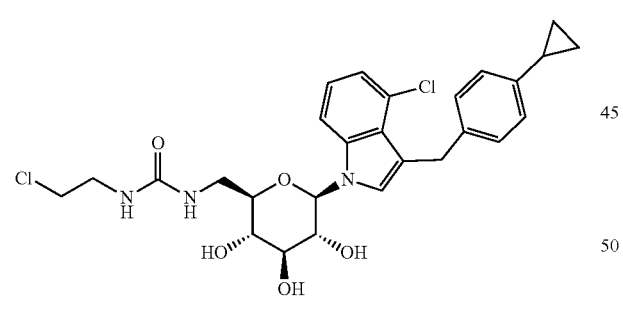
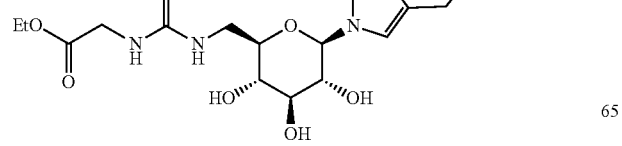

28
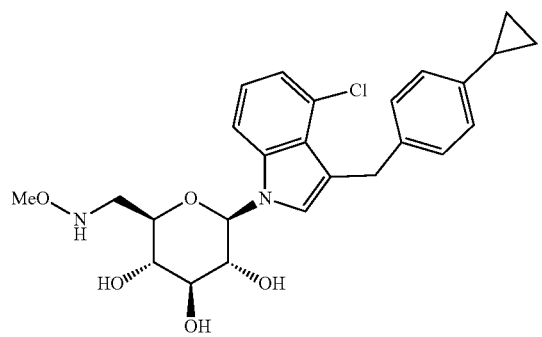
29
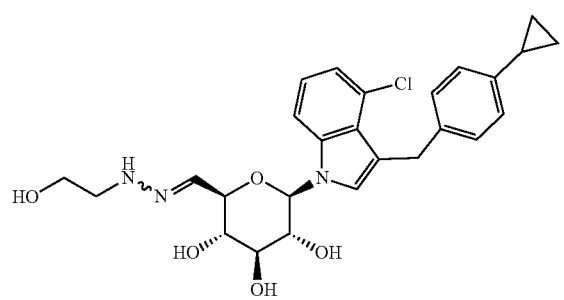
30
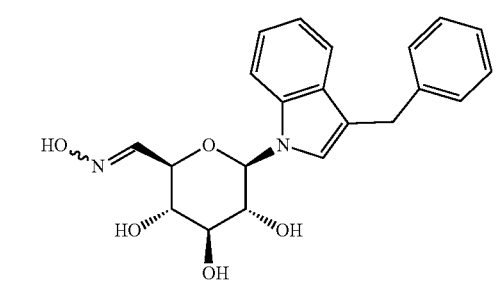
31
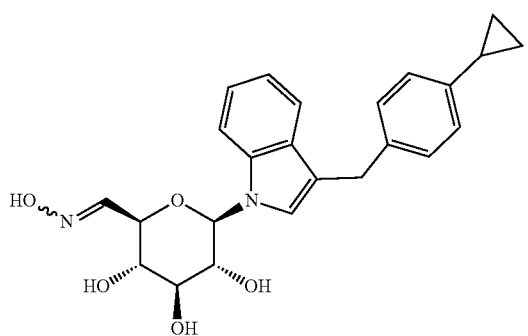
32
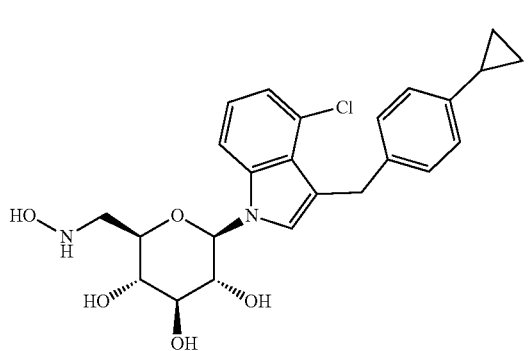
33
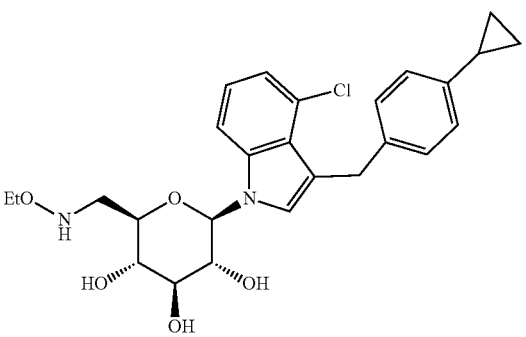
34
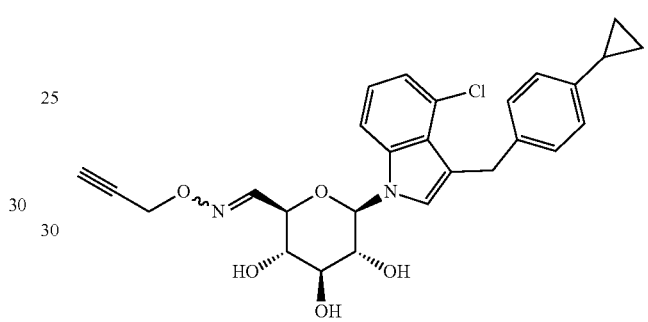
35
35
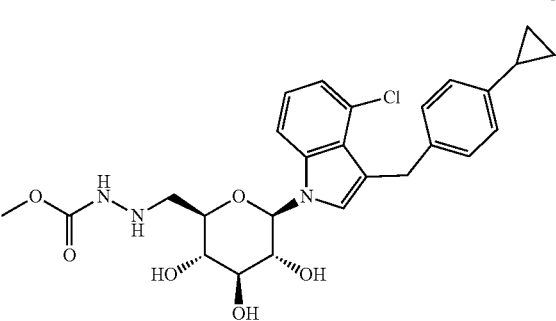
36

37
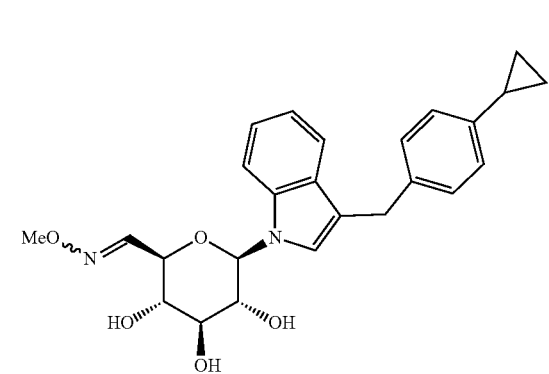
38
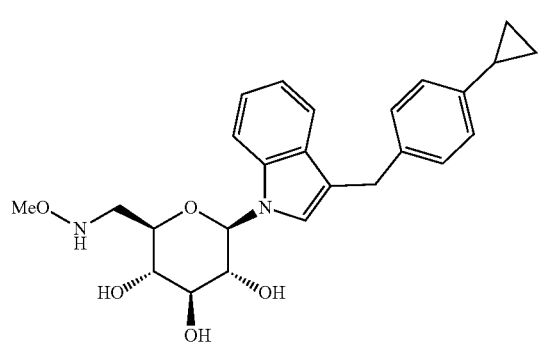
39
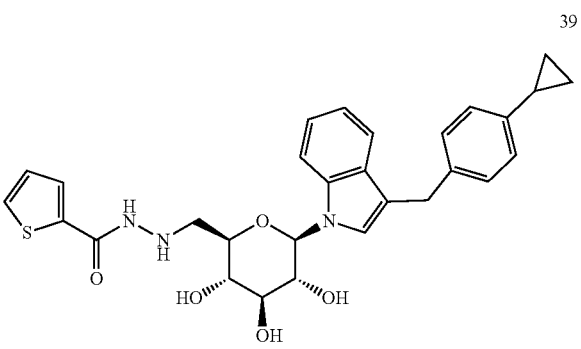
40
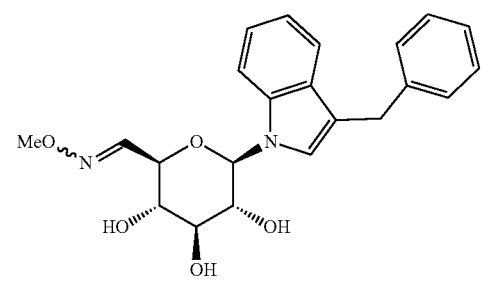
41
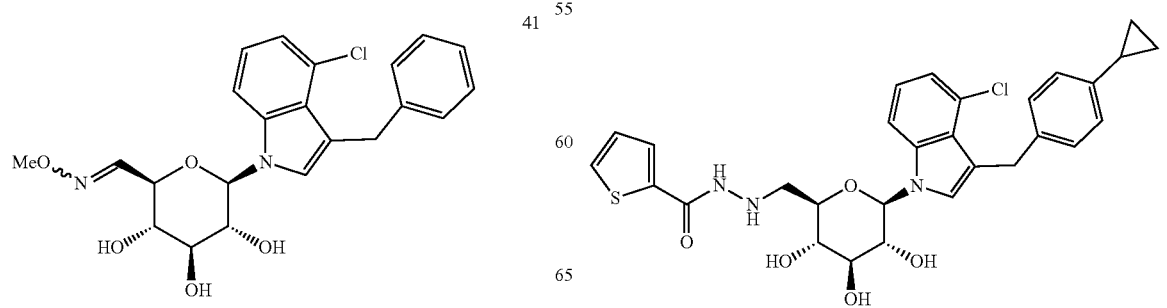
42
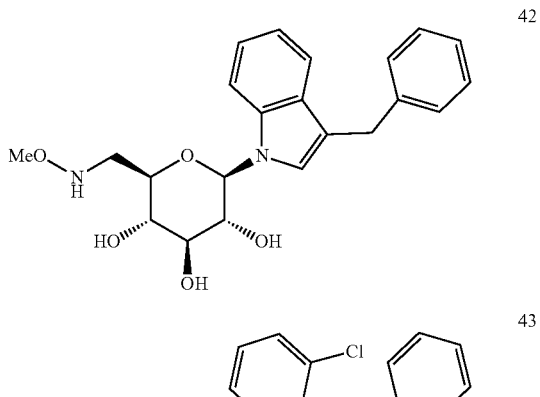
43
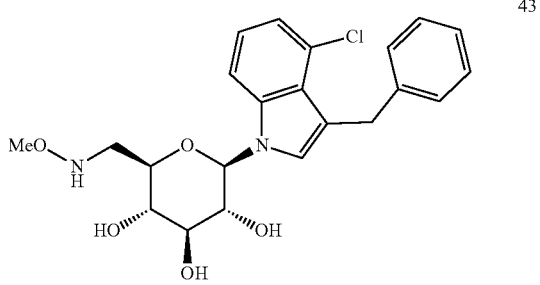
44
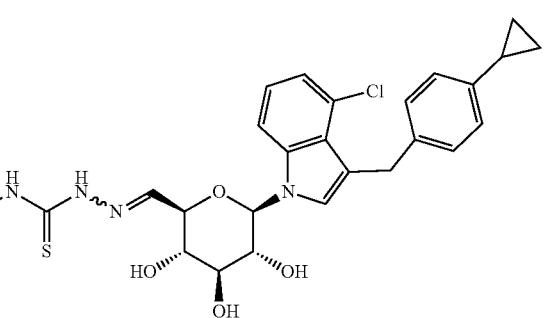
45
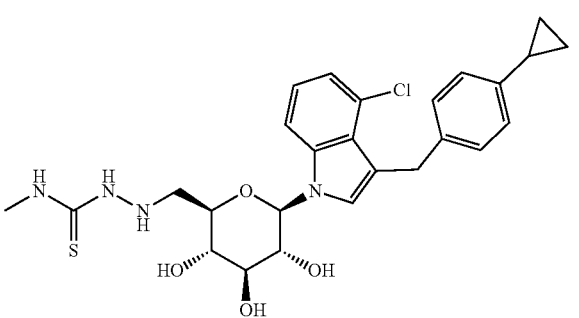
46
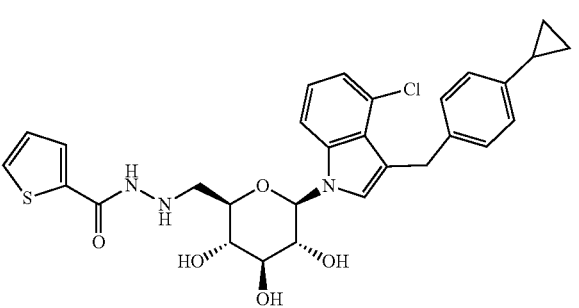

47
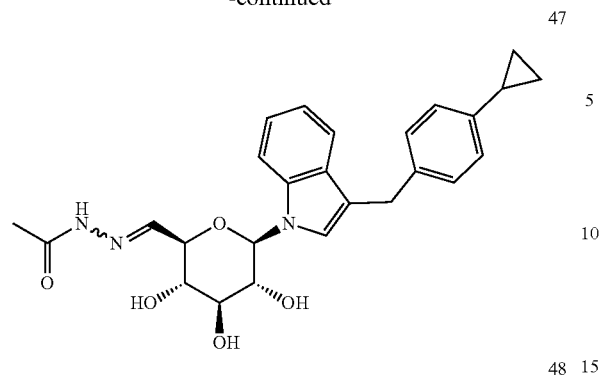
52
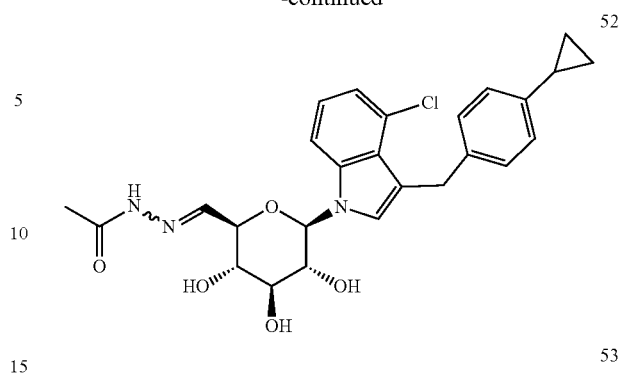
48
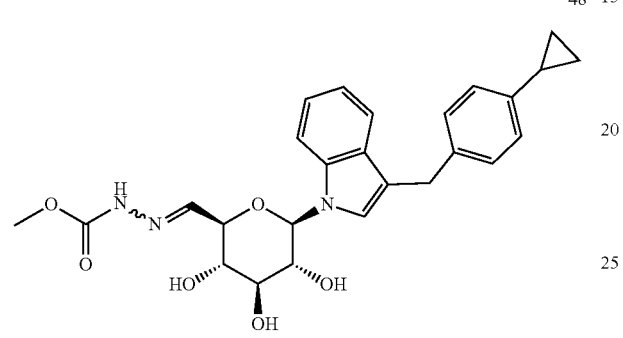
53
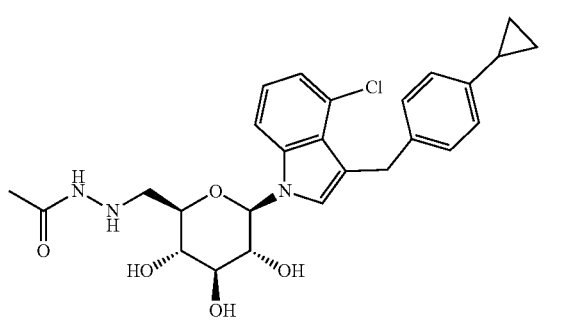
49
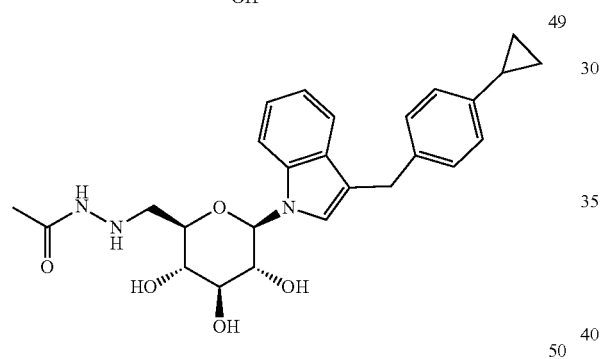
54
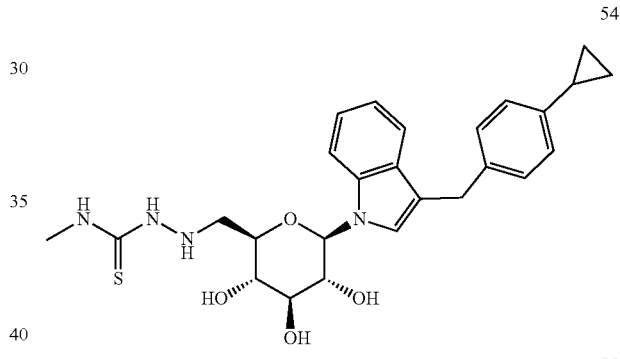
50
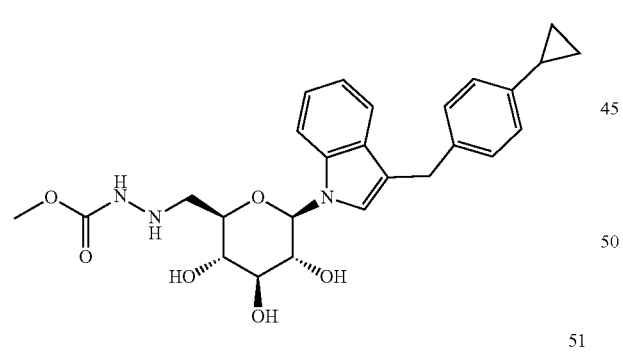
55
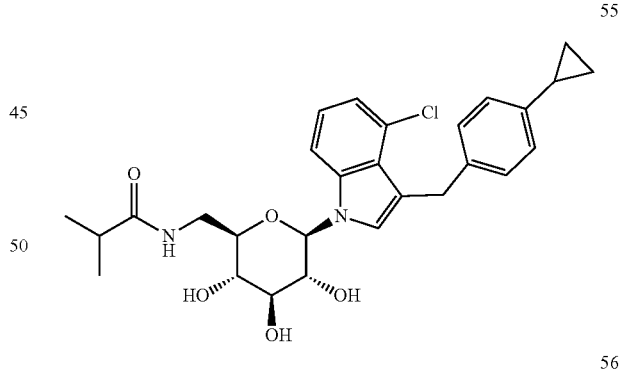
51
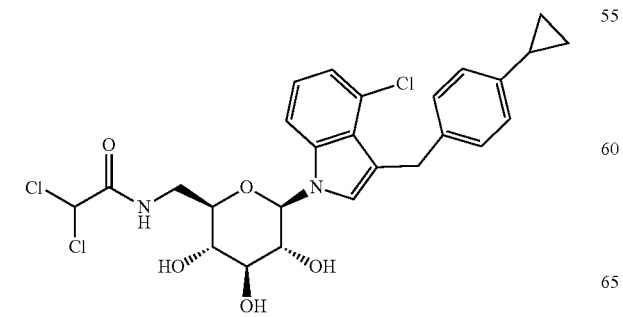
56
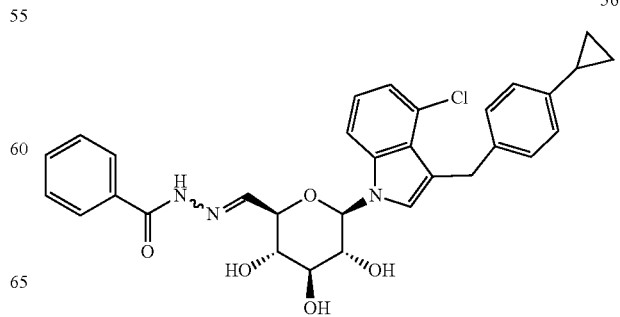

17
-continued
57
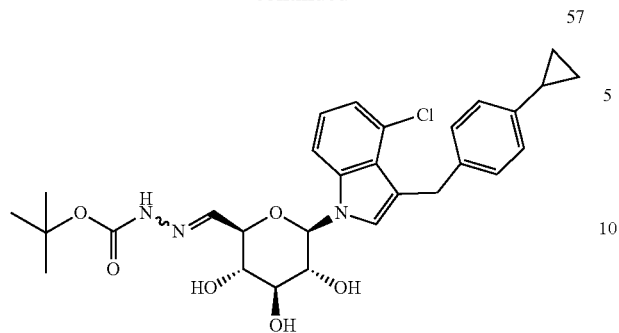
58
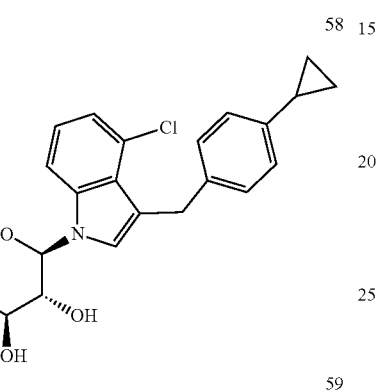
59
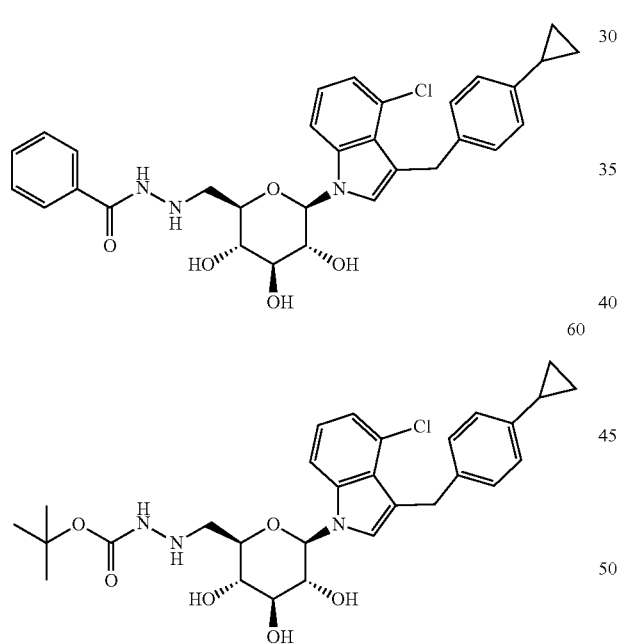
60
61
18
-continued
62
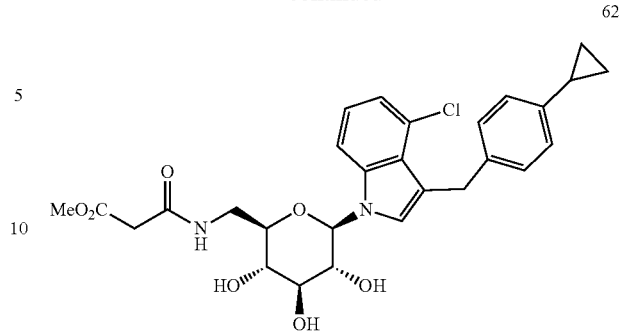
62'
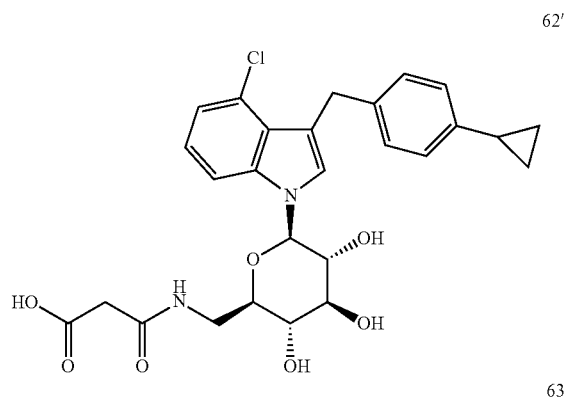
63
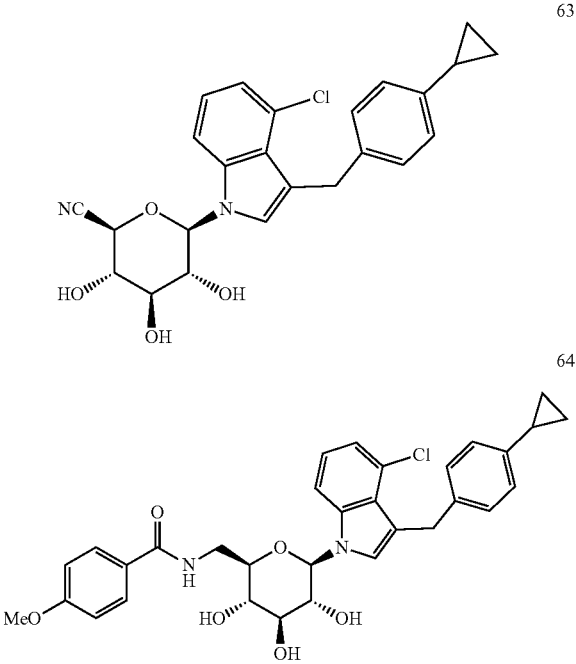
64
65

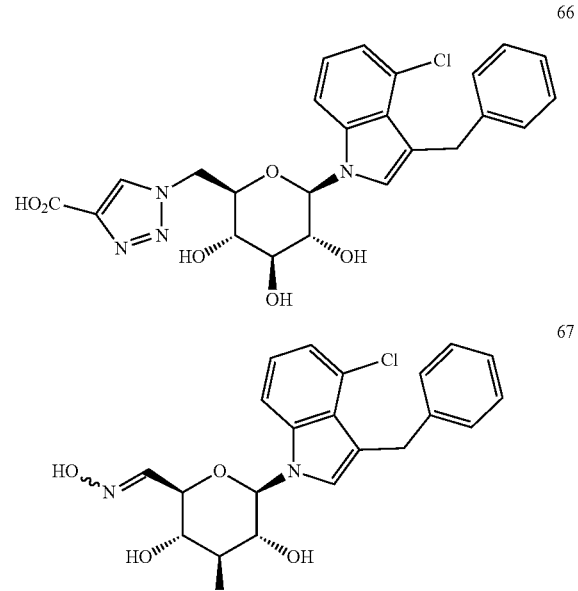
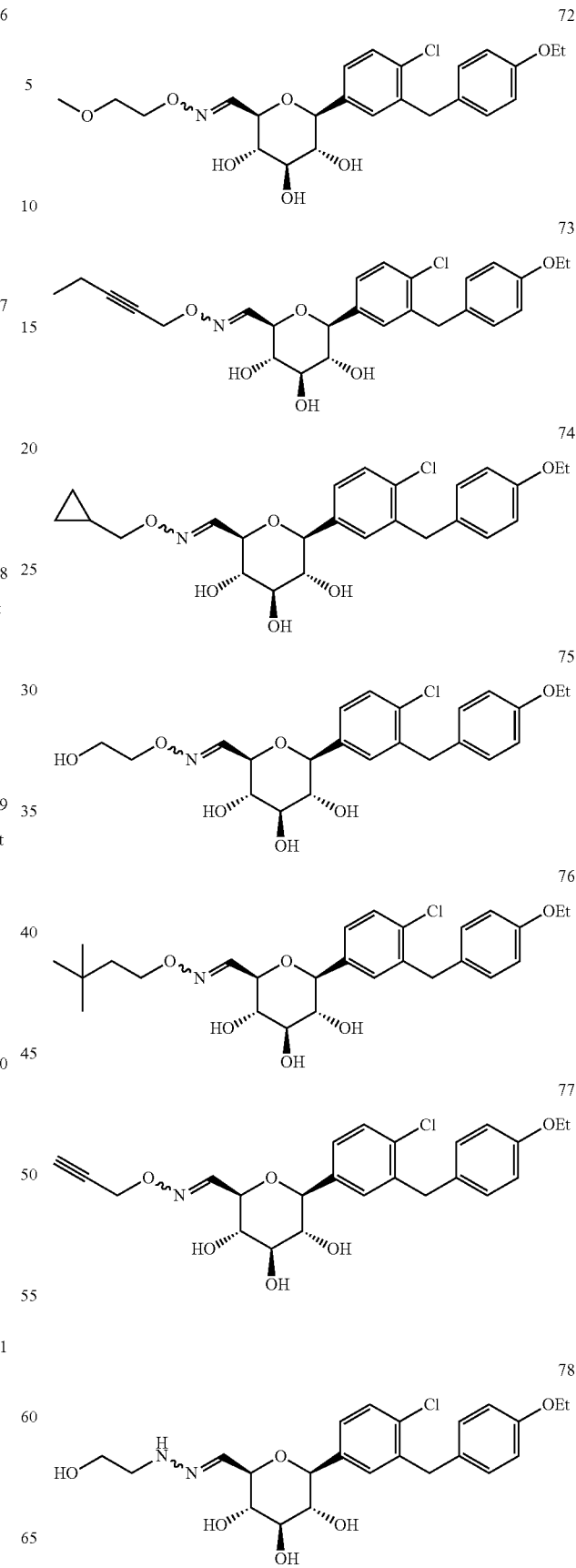

79
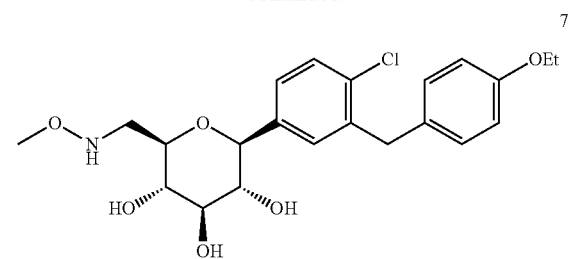
80
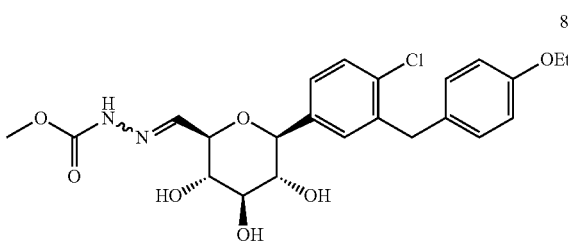
81
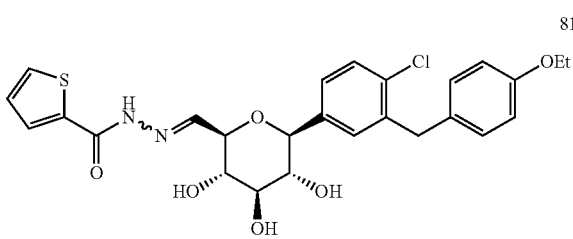
82
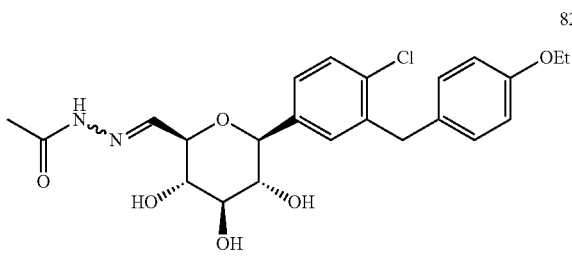
83
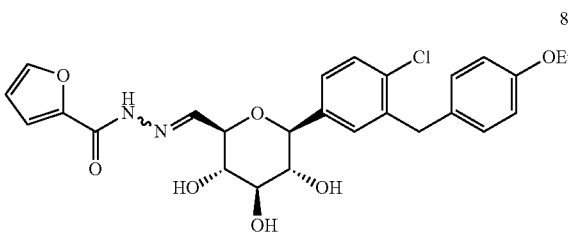
84
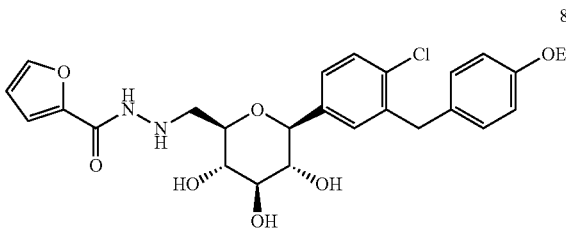
85
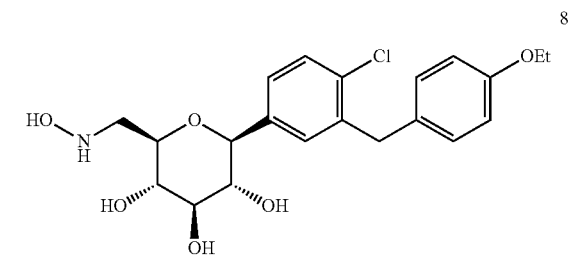
86
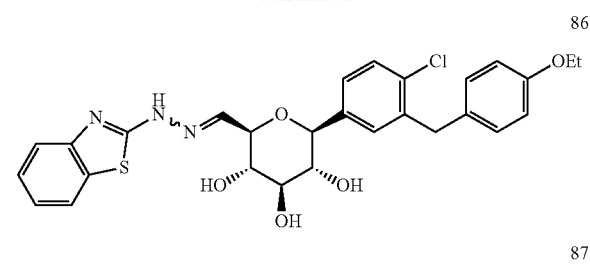
87
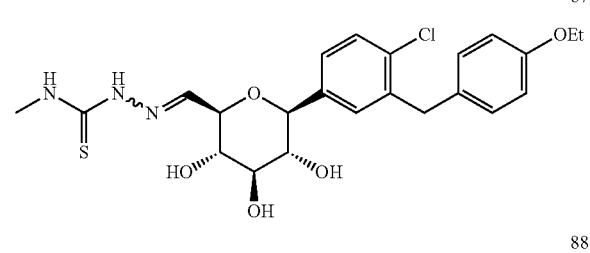
88
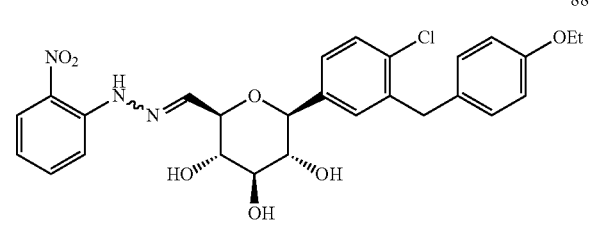
89
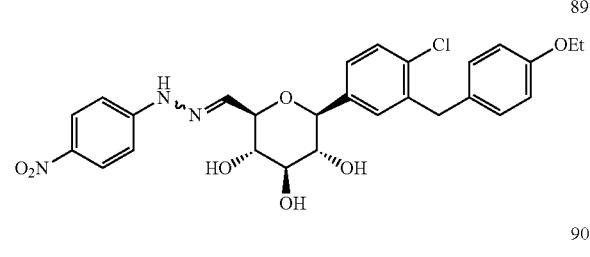
90
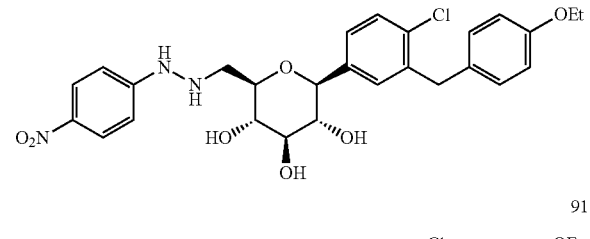
91
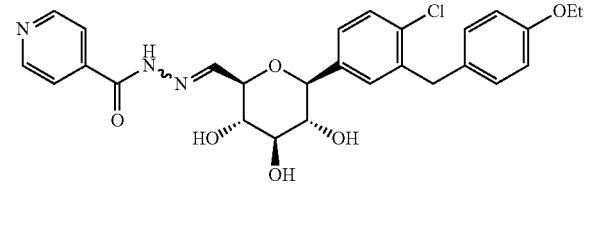
92
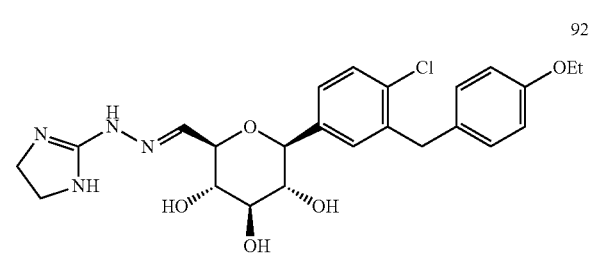

93
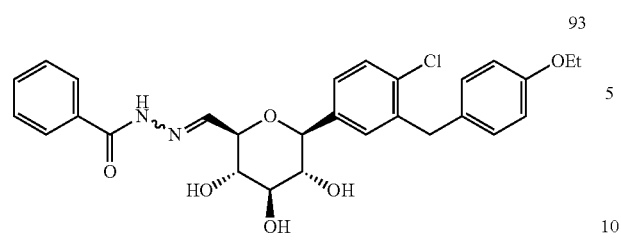
94
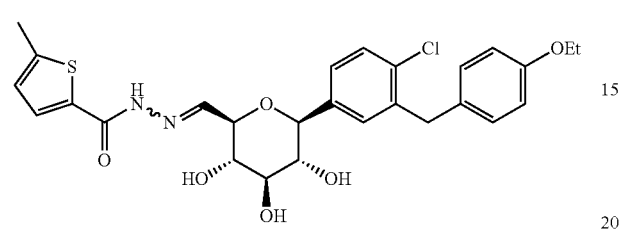
95
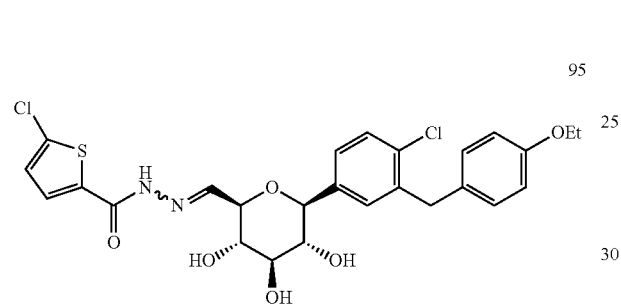
96
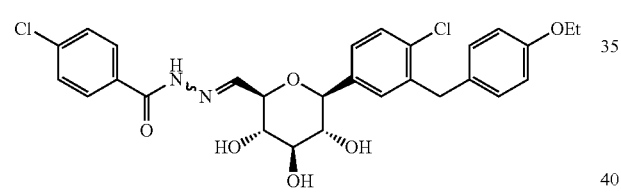
97
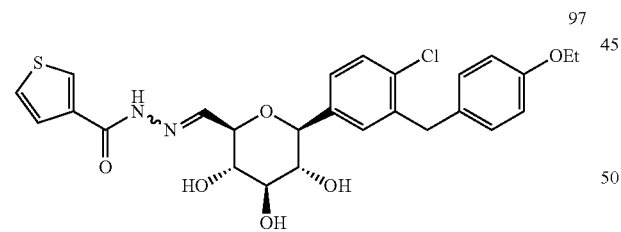
98
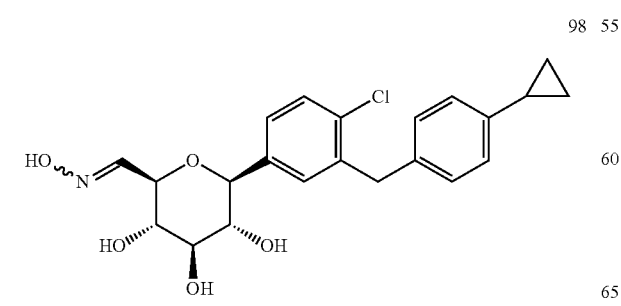
99
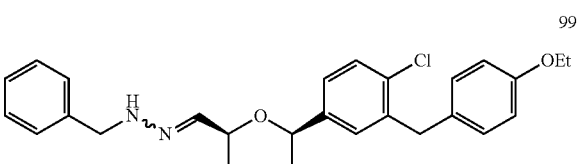
100
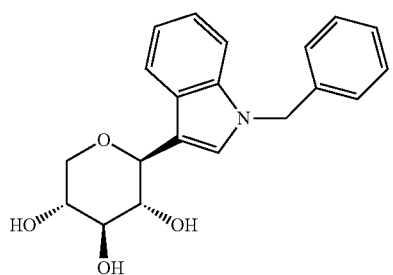
101
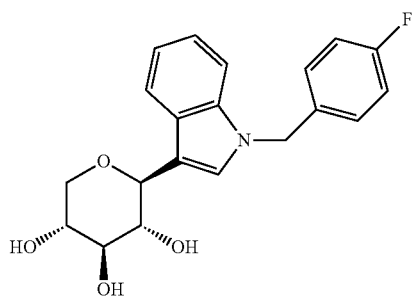
102
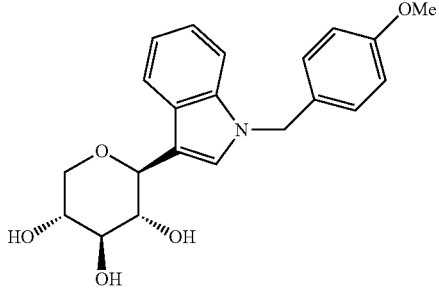
103
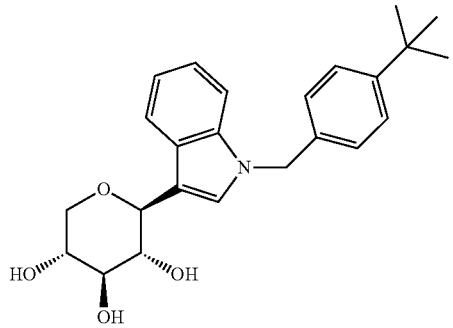

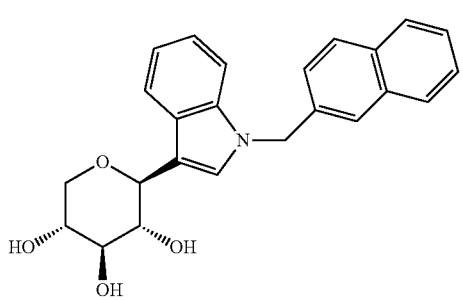
104
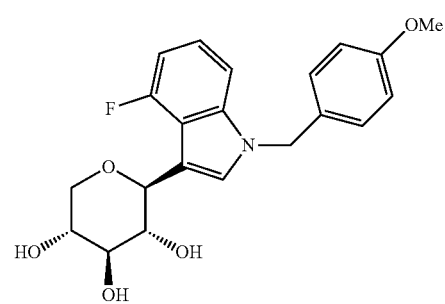
105
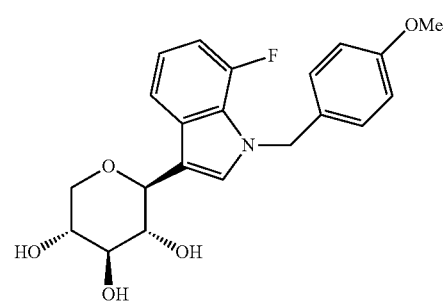
106
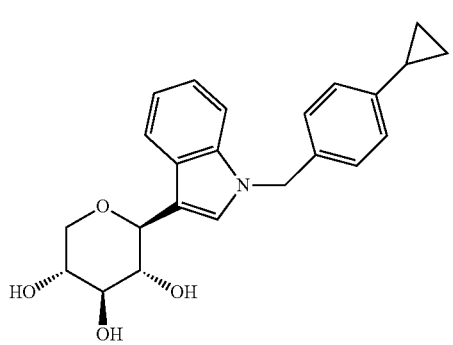
107
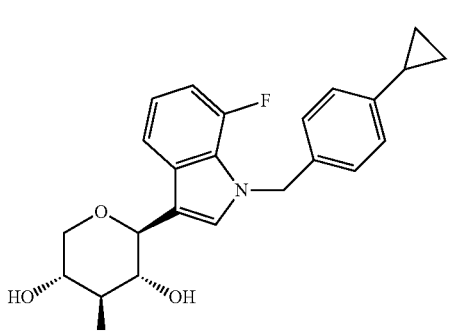
108
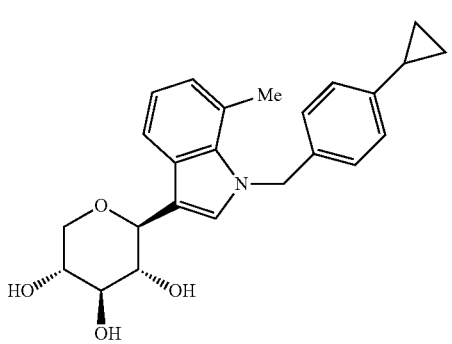
109
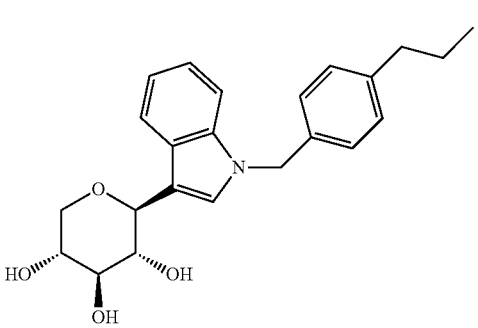
110
The glycoside compounds described herein can be prepared by methods well known in the art. The route shown in Scheme 1 below exemplifies synthesis of glycoside compounds of formula (II) of this invention.

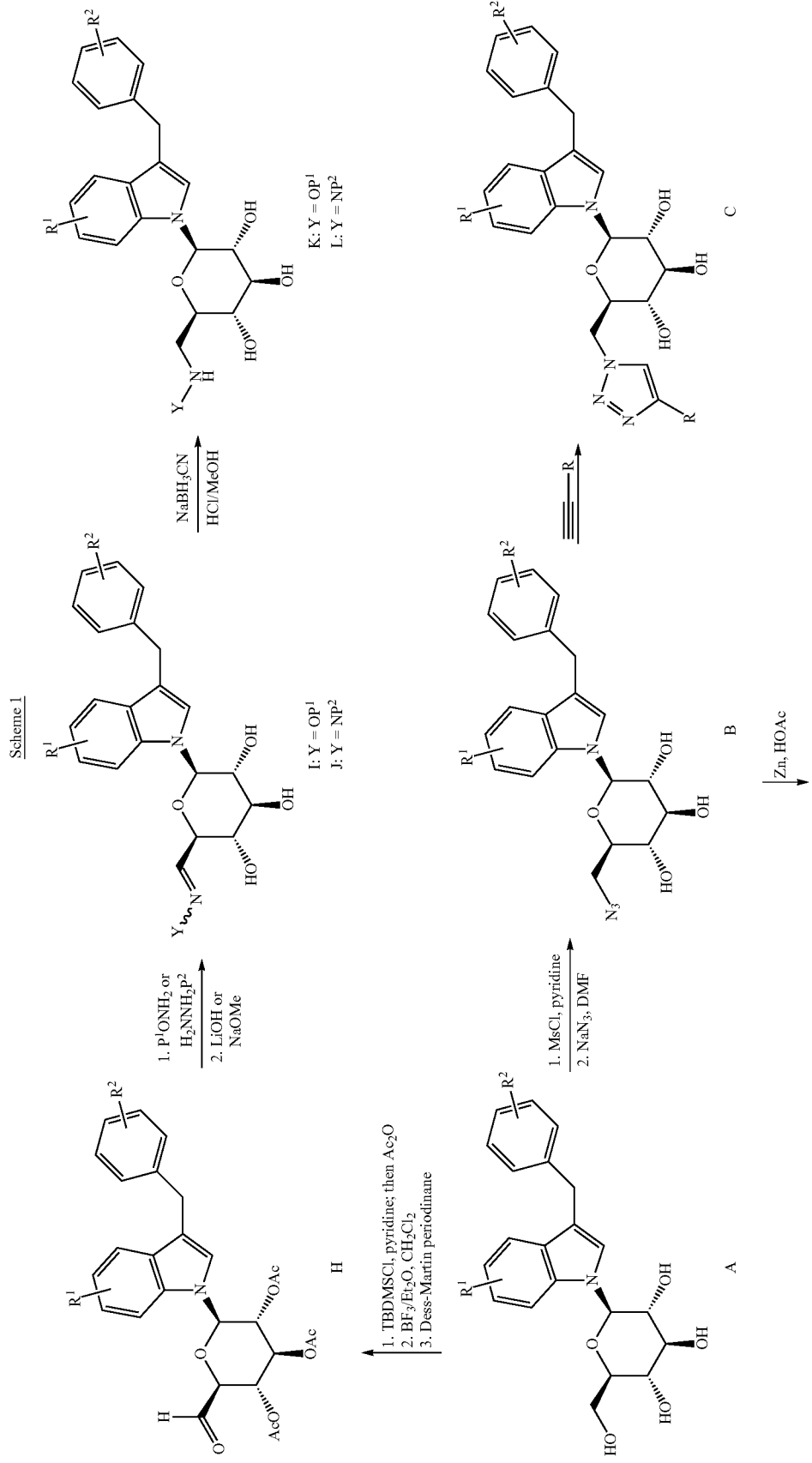

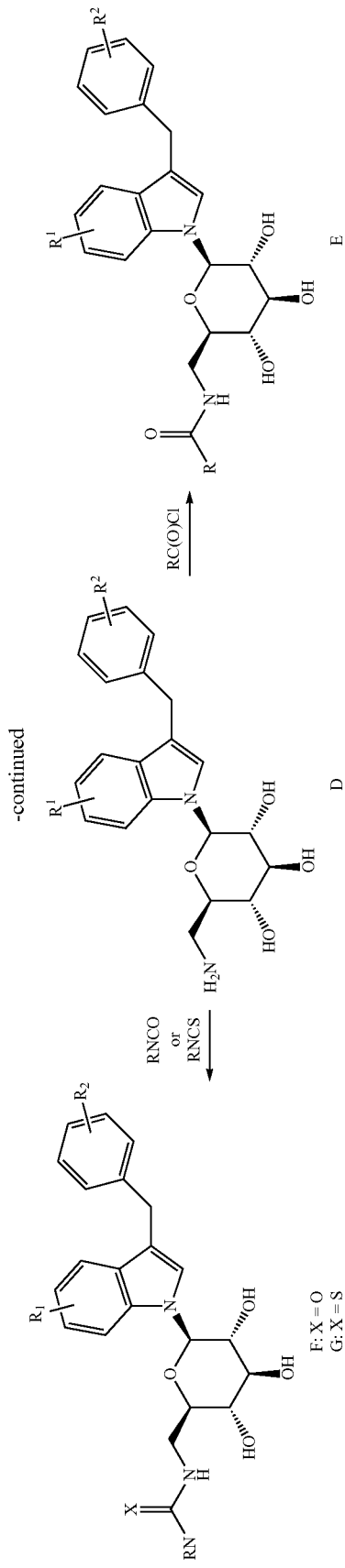

Specifically, under treatment with methanesulfonyl chloride (MsCl) in pyridine, Compound A is converted into the corresponding 6-OMs N-glycoside, which is sequentially reacted with sodium azide (NaN$_3$) to afford a 6-azido compound (Compound B). In the presence of a copper catalyst, Compound B further reacts with an alkyne to form a 1,2,3-triazole derivative (Compound C). The azido group of Compound B can be reduced by Zn/HOAc in THF to form a primary amine (Compound D), followed by amide formation with a variety of acyl chloride to obtain a 6-amide derivative (Compound E). Reacting Compound D with an isocyanate or an isothiocyanate affords a urea (Compound F) and a thiourea (Compound G), respectively.

On the other hand, Compound A can be converted into an aldehyde (Compound H) in three steps: (1) the primary alcohol group of Compound A is selectively protected by reacting with tert-butylchlorodimethylsilane (TBDMSCl) in pyridine at 85° C. for 2 h, followed by the addition of an acetic anhydride to obtain a fully protected glycoside, (2) subsequent desilylation under an acidic condition (e.g., BF$_3$.Et$_2$O) results in formation of a free primary alcohol at 6-position, and (3) the free primary alcohol is converted to the desired aldehyde (Compound H) by a Dess-Martin reagent. Condensation of (Compound H) with a hydroxylamine in pyridine followed by deacetylation gives rise to an oxime (Compound I). In a similar fashion, a hydrazone (Compound J) can be also successfully synthesized. Additionally, treatment of Compound I or Compound J with sodium cyanoborohydride (NaBH$_3$CN) under an acidic condition (e.g., HCl/MeOH) provides an N-alkylhydroxylamine (Compound K) and a hydrazine (Compound L), respectively.

The glycoside compounds of formula (I) can be prepared following the synthetic route shown in Scheme 2 below:

Scheme 2

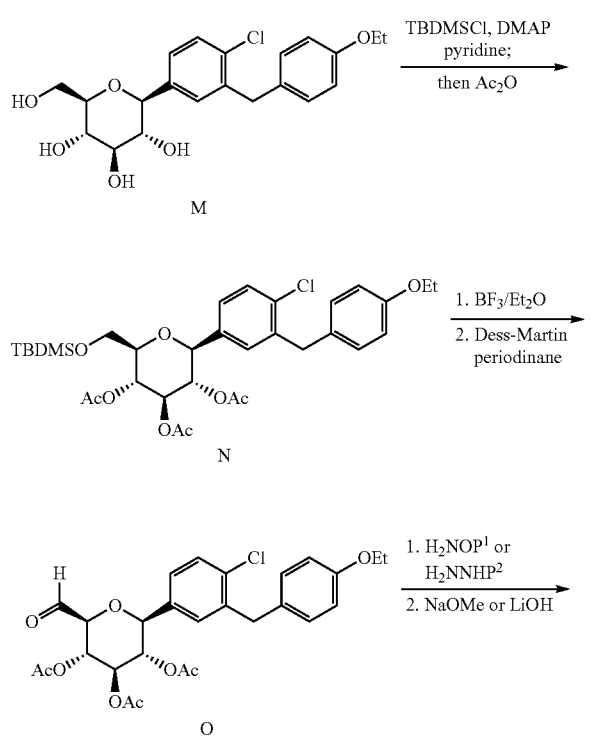

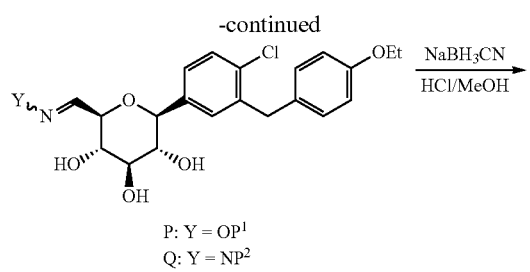

P: Y = OP$^1$
Q: Y = NP$^2$

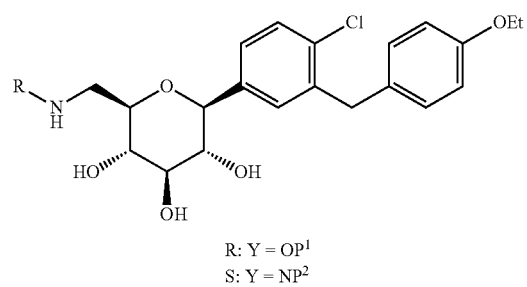

R: Y = OP$^1$
S: Y = NP$^2$

A fully protected β-C-glycoside (Compound N) can be prepared in an one-pot reaction, involving regioselective 6-O-silylation and per-O-acetylation of Compound M. More specifically, selective O-silylation of 6-OH is accomplished by reacting Compound N with tert-butylchlorodimethylsilane (TBDMSCl) in the presence of a catalytic amount of 4-N,N-dimethylaminopyridine (DMAP), followed by the addition of acetic anhydride (Ac$_2$O) to obtain fully protected β-C-glycoside (Compound N).

Compound N reacts with BF$_3$.Et$_2$O in CH$_2$Cl$_2$ to yield a primary alcohol, which is later oxidized by Dess-Martin periodinane to afford an aldehyde (Compound O). Compound O can be coupled with a hydroxylamine or a hydrazine, followed by a deacetylation step, to obtain an oxime (Compound P) or a hydrazone (Compound Q) respectively. Further reduction of Compound P or Compound Q with sodium cyanoborohydride (NaBH$_3$CN) under an acidic condition provides hydroxylamine R and hydrazine S, respectively.

The route shown in Scheme 3 below exemplifies the synthesis of the glycoside compounds of formula (III) of this invention.

Scheme 3

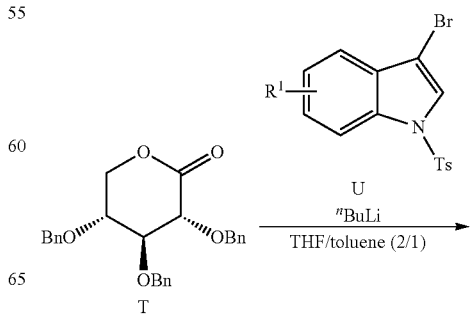

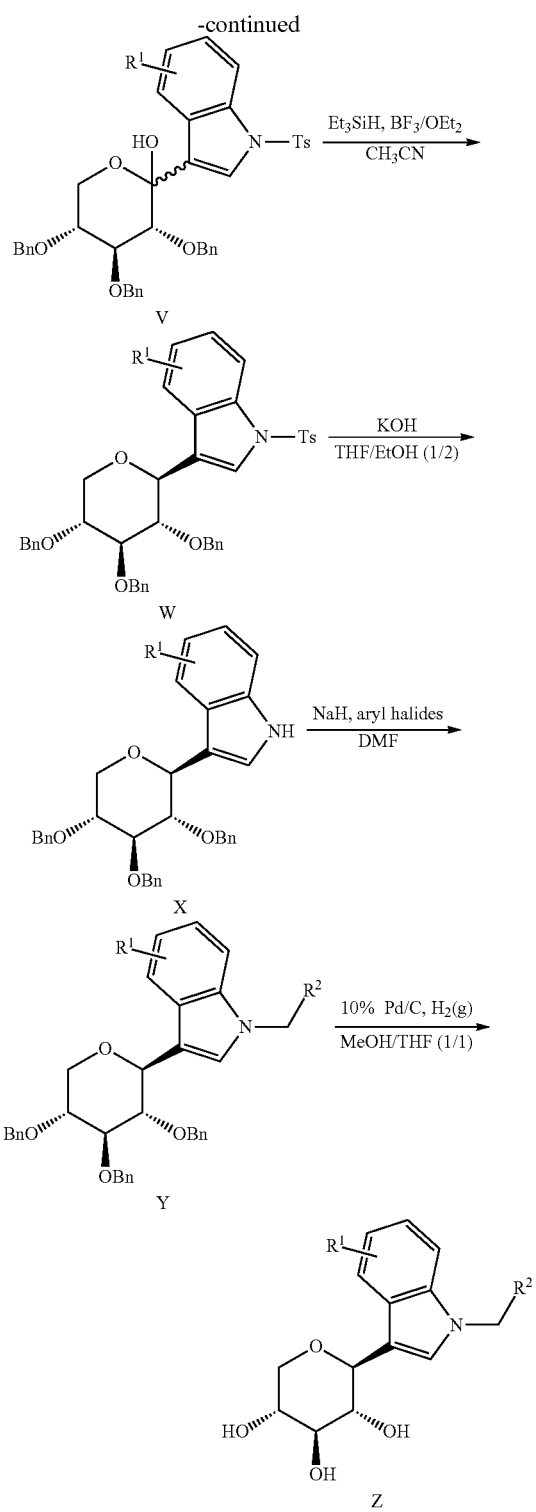

After lithium halogen exchange, an indole (Compound U) reacts with 2,3,4-tri-O-benzyl-D-xylonolactone (Compound T) to obtain a mixture of lactols (Compound V). It is subsequently reduced by triethylsilane (Et₃SiH) and boron trifluoride etherate (BF₃.Et₂O) to provide a C-linked β-xyloside (Compound W).

The tosyl group of compound W can be removed by using potassium hydroxide (KOH) in a mixed solvent of THF and EtOH at 60° C. to afford a free indole (Compound X). Under a basic condition (e.g., NaH), Compound X can be coupled with an aryl halide to give a diarylmethane (Compound Y), which in turn undergoes hydrogenolysis of the benzyl ethers over 10% Pd/C in MeOH/THF to provide a β-linked C-indolylxyloside (Compound Z).

A glycoside compound thus synthesized can be purified by any suitable method, such as column chromatography, high-pressure liquid chromatography, or recrystallization.

Of note, other glycoside compounds of this invention can be prepared using other suitable starting materials through the above-described synthetic routes and others known in the art. The methods set forth above may also additionally include steps to add or remove suitable protecting groups in order to ultimately allow synthesis of the glycoside compounds. In addition, various synthetic steps may be performed in an alternate sequence or order to give the desired compounds. Synthetic chemistry transformations and protecting group methodologies (protection and deprotection) useful in synthesizing applicable glycoside compounds are known in the art and include, for example, those described in R. Larock, *Comprehensive Organic Transformations*, VCH Publishers (1989); T. W. Greene and P. G. M. Wuts, *Protective Groups in Organic Synthesis*, $2^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The glycoside compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention is a pharmaceutical composition containing an effective amount of at least one glycoside compound described above and a pharmaceutical acceptable carrier.

Further, this invention covers a method of administering an effective amount of one or more of the glycoside compounds to a patient having a disorder described in the summary section above. "An effective amount" refers to the amount of an active glycoside compound that is required to confer a therapeutic effect on the treated subject. Effective doses will vary, as recognized by those skilled in the art, depending on the types of diseases treated, route of administration, excipient usage, and the possibility of co-usage with other therapeutic treatment.

To practice the method of the present invention, a composition having one or more glycoside compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions.

These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active glycoside compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active glycoside compound. Examples of other carriers include colloidal silicon oxide, magnesium stearate, cellulose, sodium lauryl sulfate, and D&C Yellow #10.

The glycoside compounds described above can be preliminarily screened for their efficacy in treating above-described diseases by an in vitro assay and then confirmed by animal experiments and clinic trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1

Synthesis of Compounds 1-67

The general procedure is illustrated immediately below using compound 32 as a specific example.

4-Chloro-3-(4-cyclopropylbenzyl)-1-(β-D-glucopyranosyl)-1H-indole, the starting material shown in the scheme below, was prepared following the procedure described in EP 1803729A1.

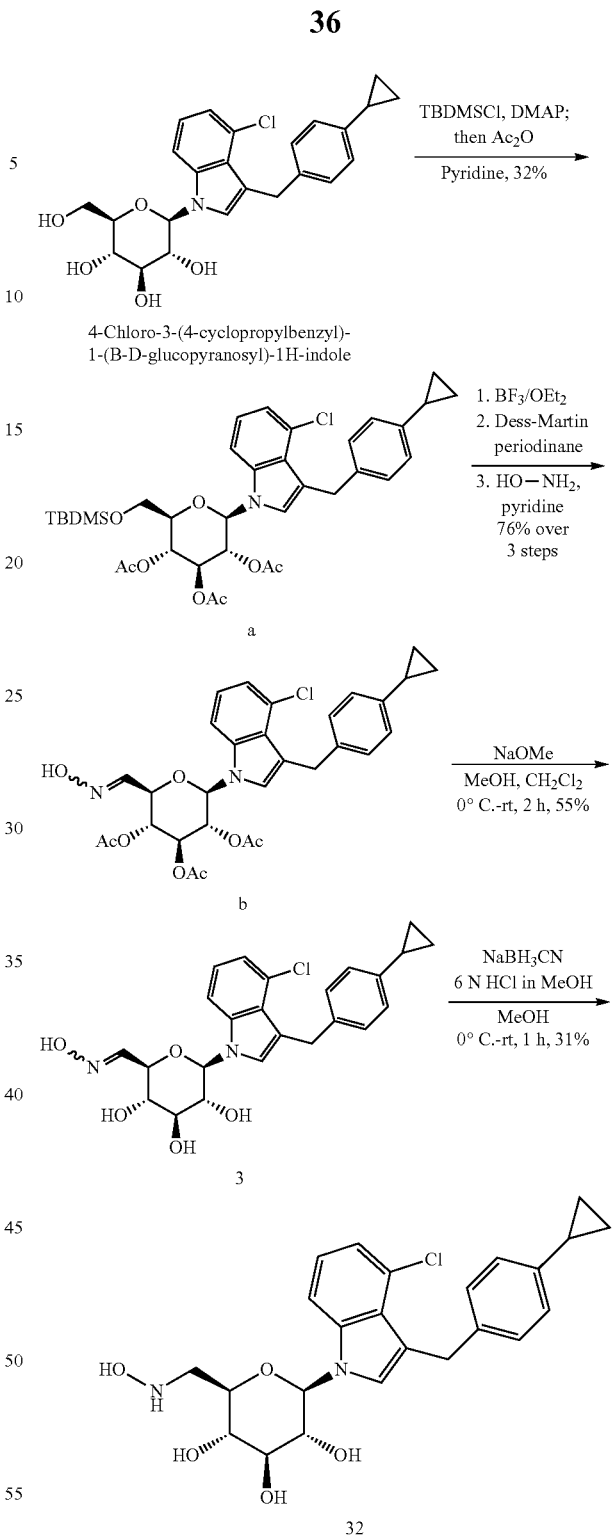

Step 1. Synthesis of Compound a

A solution of TBDMSCl (199 mg, 1.32 mmol) in pyridine (1.0 mL) was added to a solution of 4-chloro-3-(4-cyclopropylbenzyl)-1-(β-D-glucopyranosyl)-1H-indole (195 mg, 0.44 mmol) in pyridine (4.0 mL) at room temperature under nitrogen in the presence of DMAP (53.8 mg, 0.44 mmol). The reaction mixture was heated to 75° C. and stirred overnight. The reaction was cooled to room temperature, and then Ac$_2$O (0.13 mL, 1.36 mmol) was added. After 2 h stirring, the reaction was quenched by the addition of H₂O and extracted with CH₂Cl₂. The organic layer was washed with 1N HCl (aq) and saturated NaHCO₃ (aq) sequentially, dried over MgSO₄, filtered and concentrated under reduced pressure. The residue was purified by column chromatography (EtOAc/Hex=1/2) to afford Compound a (97 mg, 32%).

Step 2. Synthesis of Compound b

To a stirred solution of Compound a (97 mg, 0.14 mmol) in anhydrous CH₂Cl₂ (1.0 mL) was added BF₃.Et₂O (0.1 mL, 0.39 mmol) at 0° C. under nitrogen. After stirring at 0° C. for 20 min, the reaction was neutralized with saturated NaHCO₃ (aq). The mixture was extracted with CH₂Cl₂ and the organic phase was dried over MgSO₄, filtered and concentrated under reduced pressure. The residue was used for next step without further purification.

The residue was dissolved in CH₂Cl₂ (2.0 mL) and Dess-Martin periodinane (89.1 mg, 0.21 mmol) was added to the solution at room temperature under nitrogen. 3 h later, saturated NaHCO₃ (aq) and Na₂S₂O₃ (aq) were added to quench the reaction and the mixture was stirred for another 30 min. The mixture was extracted with CH₂Cl₂ and the organic phase was dried over MgSO₄, filtered and concentrated under reduced pressure. The thus-obtained oxidation residue (~81 mg, ~100%) was used for next step without further purification.

To a solution of the oxidation residue (51 mg, 0.086 mmol) in pyridine (1.0 mL) was added hydroxylamine hydrochloride (7.6 mg, 0.13 mmol) at room temperature. After 2 h, the solvent was removed under reduced pressure. The residue was re-dissolved in CH₂Cl₂ and washed with H₂O. The organic phase was dried over MgSO₄, filtered and concentrated under reduced pressure. Purification by column chromatography (EtOAc/Hex=1/2) yielded Compound b (40 mg, 76% over 3 steps, cis/trans-isomers).

Step 3. Synthesis of Compound 3

A 30% solution of NaOMe in MeOH (40 µL) was added to a solution of Compound b (40 mg, 0.069 mmol) in MeOH/CH₂Cl₂ (v/v, 2/1, 3.0 mL) at 0° C. under nitrogen. The reaction was warmed up to room temperature gradually and then neutralized with acidic resin after 2 h. The reaction mixture was filtered and the filtrate was concentrated under reduced pressure. The residue was purified by column chromatography (MeOH/CH₂Cl₂=1/20) to give the desired product Compound 3 (17.3 mg, 55%, cis/trans-isomers) as a white solid.

Compound 3: $^1$H NMR (400 MHz, CD₃OD, major isomer) δ 7.44 (d, 1H), 7.31 (d, 1H), 7.10-7.05 (m, 3H), 7.00-6.95 (m, 4H), 5.46 (d, 1H), 4.28 (s, 2H), 4.08 (dd, 1H), 3.83 (t, 1H), 3.58 (t, 1H), 3.53 (t, 1H), 1.88-1.81 (m, 1H), 0.92-0.86 (m, 2H), 0.64-0.60 (m, 2H); LC-MS (ESI) m/z 457/459 (Chlorine) (MH⁺) & 479/481 (Chlorine) (MNa⁺).

Step 4. Synthesis of Compound 32

To a stirred solution of Compound 3 (12 mg, 0.026 mmol) in MeOH (1.0 mL) at 0° C. was added NaBH₃CN (3.3 mg, 0.052 mmol) and then 6 N HCl in MeOH until the pH value of the solution is in the range of 1-3. The reaction was warmed up to room temperature and stirred for 1 h. The reaction was neutralized by the addition of saturated NaHCO₃ (aq) and the resulting mixture was extracted with CH₂Cl₂. The organic phase was dried over MgSO₄, filtered and concentrated under reduced pressure. The residue was purified by column chromatography (MeOH/CH₂Cl₂=1/10) to afford Compound 32 (3.7 mg, 31%).

Compound 32: $^1$H NMR (400 MHz, CD₃OD) δ 7.46 (dd, 1H), 7.11-7.06 (m, 3H), 7.02-6.95 (m, 4H), 5.39 (d, 1H), 4.28 (s, 2H), 3.85-3.79 (m, 2H), 3.55 (t, 1H), 3.36-3.33 (m, 2H), 2.91 (dd, 1H), 1.89-1.82 (m, 1H), 0.93-0.88 (m, 2H), 0.65-0.61 (m, 2H); LC-MS (ESI) m/z 459/461 (Chlorine) (M+H⁺) & 481/483 (Chlorine) (M+Na⁺).

Compounds 1, 2, 4-31 and 33-67 were prepared in a manner similar to that described immediately above and in Scheme 1. Of note, oximes or hydrazones were isolated as a mixture of cis/trans-isomers. The NMR assignments of these compounds were based on the characters of major isomers.

Compound 1: $^1$H NMR (400 MHz, CD₃OD) δ 7.45 (d, 1H), 7.10-6.93 (m, 7H), 5.41 (d, 1H), 4.27 (s, 2H), 3.79 (t, 1H), 3.71-3.67 (m, 1H), 3.61-3.45 (m, 3H), 3.40 (dd, 1H), 1.87-1.81 (m, 1H), 0.92-0.86 (m, 2H), 0.63-0.59 (m, 2H); LC-MS (ESI) m/z 469/471 (Chlorine) (MH⁺) & 491/493 (Chlorine) (MNa⁺).

Compound 2: $^1$H NMR (300 MHz, CD₃OD) δ 7.47 (dd, 1H), 7.13-7.07 (m, 3H), 7.05-7.01 (m, 2H), 6.98-6.95 (m, 2H), 5.44 (d, 1H), 4.29 (s, 2H), 3.85 (t, 1H), 3.66 (ddd, 1H), 3.57 (t, 1H), 3.37-3.35 (m, 1H), 3.26 (dd, 1H), 2.91 (dd, 1H), 1.89-1.83 (m, 1H), 0.95-0.88 (m, 2H), 0.66-0.60 (m, 2H); LC-MS (ESI) m/z 443/445 (Chlorine) (MH⁺) & 465/467 (Chlorine) (MNa⁺).

Compound 4: $^1$H NMR (400 MHz, CD₃OD) δ 7.43 (d, 1H), 7.31 (d, 1H), 7.10-7.05 (m, 3H), 7.01-6.93 (m, 4H), 5.46 (d, 1H), 4.27 (s, 2H), 4.09 (dd, 1H), 3.84 (t, 1H), 3.80 (s, 3H), 3.58 (t, 1H), 3.52 (t, 1H), 1.87-1.80 (m, 1H), 0.91-0.85 (m, 2H), 0.63-0.59 (m, 2H); LC-MS (ESI) m/z 471/473 (Chlorine) (MH⁺) & 493/495 (Chlorine) (MNa⁺).

Compound 5: $^1$H NMR (400 MHz, CD₃OD) δ 7.44 (dd, 1H), 7.32 (d, 1H), 7.11-7.06 (m, 3H), 7.02-6.95 (m, 4H), 5.47 (d, 1H), 4.28 (s, 2H), 4.12-4.05 (m, 3H), 3.85 (t, 1H), 3.60 (t, 1H), 3.53 (t, 1H), 1.87-1.81 (m, 1H), 1.20 (t, 3H), 0.92-0.88 (m, 2H), 0.64-0.60 (m, 2H); LC-MS (ESI) m/z 485/487 (Chlorine) (MH⁺) & 507/509 (Chlorine) (MNa⁺).

Compound 6: $^1$H NMR (400 MHz, CD₃OD) δ 8.04 (s, 1H), 7.07-7.03 (m, 3H), 7.01-6.92 (m, 5H), 5.35 (d, 1H), 4.83 (dd, 1H), 4.49 (dd, 1H), 4.24 (s, 2H), 3.90 (ddd, 1H), 3.80 (s, 3H), 3.82-3.76 (m, 1H), 3.58 (t, 1H), 3.30-3.26 (m, 1H), 1.85-1.79 (m, 1H), 0.91-0.87 (m, 2H), 0.63-0.59 (m, 2H); LC-MS (ESI) m/z 553/555 (Chlorine) (MH⁺) & 575/577 (Chlorine) (MNa⁺).

Compound 7: $^1$H NMR (400 MHz, CD₃OD) δ 8.12 (s, 1H), 7.09-7.05 (m, 3H), 7.01-6.93 (m, 5H), 5.37 (d, 1H), 4.84 (dd, 1H), 4.59 (dd, 1H), 4.25 (s, 2H), 3.93 (ddd, 1H), 3.78 (t, 1H), 3.58 (t, 1H), 3.30-3.25 (m, 1H), 1.87-1.81 (m, 1H), 0.92-0.83 (m, 2H), 0.64-0.60 (m, 2H); LC-MS (ESI) m/z 539/541 (Chlorine) (MH⁺) & 561/563 (Chlorine) (MNa⁺).

Compound 8: $^1$H NMR (400 MHz, CD₃OD) δ 7.30 (s, 1H), 7.13 (dd, 1H), 7.10-6.94 (m, 7H), 5.36 (d, 1H), 4.74 (dd, 1H), 4.45 (dd, 1H), 4.27 (s, 2H), 3.86 (ddd, 1H), 3.79 (t, 1H), 3.57 (t, 1H), 3.25 (dd, 1H), 1.87-1.79 (m, 2H), 0.92-0.85 (m, 4H), 0.64-0.58 (m, 4H); LC-MS (ESI) m/z 535/537 (Chlorine) (MH⁺) & 557/559 (Chlorine) (MNa⁺).

Compound 9: $^1$H NMR (400 MHz, CD₃OD) δ 7.17 (dd, 1H), 7.09-7.06 (m, 3H), 7.04-6.99 (m, 3H), 6.97-6.94 (m, 2H), 5.39 (d, 1H), 4.71 (dd, 1H), 4.42 (dd, 1H), 4.27 (s, 2H), 3.93-3.79 (m, 4H), 3.58 (t, 1H), 3.30-3.25 (m, 1H), 1.86-1.82 (m, 1H), 1.26 (t, 3H), 0.93-0.88 (m, 2H), 0.64-0.60 (m, 2H); LC-MS (ESI) m/z 539/541 (Chlorine) (MH⁺) & 561/563 (Chlorine) (MNa⁺).

Compound 10: $^1$H NMR (400 MHz, CD₃OD) δ 7.34 (s, 1H), 7.18-7.14 (m, 1H), 7.08-7.06 (m, 2H), 7.02-6.98 (m, 3H), 6.95-6.93 (m, 2H), 5.38 (d, 1H), 4.77 (dd, 1H), 4.44 (dd, 1H), 4.28, 4.26 (ABq, 2H), 3.86 (ddd, 1H), 3.81 (t, 1H), 3.58 (t, 1H), 3.27 (t, 1H), 3.01 (quint, 1H), 1.96-1.91 (m, 2H), 1.87-1.80 (m, 1H), 1.65-1.56 (m, 4H), 1.49-1.40 (m, 2H), 0.92-0.87 (m, 2H), 0.63-0.59 (m, 2H); LC-MS (ESI) m/z 563/565 (Chlorine) (MH⁺) & 585/587 (Chlorine) (MNa⁺).

Compound 11: ¹H NMR (400 MHz, CD₃OD) δ 7.44 (dd, 1H), 7.11-7.07 (m, 3H), 7.03-6.96 (m, 4H), 5.39 (d, 1H), 4.28 (s, 2H), 3.81 (t, 1H), 3.68 (dd, 1H), 3.60-3.53 (m, 2H), 3.34-3.26 (m, 2H), 1.89 (s, 3H), 1.89-1.83 (m, 1H), 0.93-0.89 (m, 2H), 0.65-0.61 (m, 2H); LC-MS (ESI) m/z 485/487 (Chlorine) (MH⁺) & 507/509 (Chlorine) (MNa⁺).

Compound 12: ¹H NMR (400 MHz, CD₃OD) δ 7.42 (dd, 1H), 7.10-6.94 (m, 7H), 6.80-6.71 (m, 1H), 5.91-5.87 (m, 1H), 5.38 (d, 1H), 4.28 (s, 2H), 3.81 (t, 1H), 3.72 (dd, 1H), 3.62-3.54 (m, 2H), 3.39 (dd, 1H), 3.30-3.25 (m, 1H), 1.87-1.80 (m, 1H), 1.81 (dd, 3H), 0.92-0.88 (m, 2H), 0.64-0.60 (m, 2H); LC-MS (ESI) m/z 511/513 (Chlorine) (MH⁺).

Compound 13: ¹H NMR (400 MHz, CD₃OD) δ 7.45 (dd, 1H), 7.10-6.94 (m, 7H), 5.39 (d, 1H), 4.28 (s, 2H), 3.82 (t, 1H), 3.68 (dd, 1H), 3.59-3.54 (m, 2H), 3.38-3.25 (m, 2H), 1.87-1.81 (m, 1H), 1.53-1.49 (m, 1H), 0.92-0.80 (m, 4H), 0.73-0.69 (m, 2H), 0.64-0.60 (m, 2H); LC-MS (ESI) m/z 511/513 (Chlorine) (MH⁺).

Compound 14: ¹H NMR (400 MHz, CD₃OD) δ 7.43 (dd, 1H), 7.11-7.06 (m, 3H), 7.02-6.96 (m, 4H), 5.38 (d, 1H), 4.28 (s, 2H), 3.81 (t, 1H), 3.76-3.69 (m, 3H), 3.61-3.54 (m, 2H), 3.37-3.29 (m, 2H), 2.60 (t, 2H), 1.88-1.81 (m, 1H), 0.94-0.88 (m, 2H), 0.65-0.61 (m, 2H); LC-MS (ESI) m/z 533/535 (Chlorine) (MH⁺) & 555/557 (Chlorine) (MNa⁺).

Compound 15: ¹H NMR (400 MHz, CD₃OD) δ 7.41 (dd, 1H), 7.13-7.07 (m, 4H), 7.02 (dd, 1H), 6.99-6.95 (m, 3H), 6.83-6.78 (m, 2H), 5.36 (d, 1H), 4.29 (s, 2H), 3.77 (t, 1H), 3.69 (dd, 1H), 3.65 (d, 2H), 3.59-3.52 (m, 2H), 3.34-3.30 (m, 1H), 3.25 (t, 1H), 1.89-1.82 (m, 1H), 0.93-0.88 (m, 2H), 0.65-0.60 (m, 2H); LC-MS (ESI) m/z 589/591 (Chlorine) (MNa⁺).

Compound 16: ¹H NMR (400 MHz, CD₃OD) δ 8.45 (d, 1H), 7.40-7.37 (m, 1H), 7.08 (d, 2H), 7.02-6.93 (m, 5H), 6.86 (d, 1H), 5.40 (d, 1H), 4.27 (s, 2H), 3.89 (dd, 1H), 3.85 (t, 1H), 3.73 (ddd, 1H), 3.58 (t, 1H), 3.48 (dd, 1H), 3.36-3.30 (m, 1H), 1.87-1.80 (m, 1H), 0.92-0.87 (m, 2H), 0.63-0.59 (m, 2H); LC-MS (ESI) m/z 560/562 (Chlorine) (MNa⁺).

Compound 17: ¹H NMR (400 MHz, CD₃OD) δ 7.43 (d, 1H), 7.10-7.06 (m, 3H), 7.04-7.00 (m, 2H), 6.96-6.94 (m, 2H), 5.39 (d, 1H), 4.28 (s, 2H), 3.98 (s, 2H), 3.82 (t, 1H), 3.75 (dd, 1H), 3.62 (ddd, 1H), 3.56 (t, 1H), 3.37-3.28 (m, 2H), 1.88-1.81 (m, 1H), 0.93-0.88 (m, 2H), 0.64-0.60 (m, 2H); LC-MS (ESI) m/z 541/543 (Chlorine) (MNa⁺).

Compound 18: ¹H NMR (400 MHz, CD₃OD) δ 7.44 (dd, 1H), 7.11-7.03 (m, 3H), 7.02-7.00 (m, 2H), 6.98-6.95 (m, 2H), 5.38 (d, 1H), 4.28 (s, 2H), 3.81 (t, 1H), 3.70 (dd, 1H), 3.62-3.54 (m, 4H), 3.37-3.30 (m, 2H), 2.72 (t, 2H), 1.89-1.82 (m, 1H), 0.93-0.88 (m, 2H), 0.65-0.61 (m, 2H); LC-MS (ESI) m/z 599/601 (Chlorine) (MNa⁺).

Compound 19: ¹H NMR (400 MHz, CD₃OD) δ 7.40 (dd, 1H), 7.25-7.22 (m, 2H), 7.16-7.05 (m, 6H), 7.13 (dd, 1H), 6.99-6.97 (m, 2H), 6.90 (s, 1H), 5.31 (d, 1H), 4.30 (s, 2H), 3.65 (t, 1H), 3.62-3.58 (m, 3H), 3.53-3.48 (m, 2H), 3.39 (dd, 1H), 3.13 (t, 1H), 1.87-1.83 (m, 1H), 0.92-0.88 (m, 2H), 0.64-0.60 (m, 2H); LC-MS (ESI) m/z 615/617 (Chlorine) (MNa⁺).

Compound 20: ¹H NMR (300 MHz, CD₃OD) δ 7.44 (dd, 1H), 7.12-6.96 (m, 7H), 5.40 (d, 1H), 4.29 (s, 2H), 3.81 (t, 1H), 3.63-3.46 (m, 5H), 3.32-3.26 (m, 2H), 3.17 (t, 2H), 1.95-1.75 (m, 3H), 0.94-0.88 (m, 2H), 0.66-0.60 (m, 2H); LC-MS (ESI) m/z 562/564 (Chlorine) (MH⁺) & 584/586 (Chlorine) (MNa⁺).

Compound 21: ¹H NMR (300 MHz, CD₃OD) δ 7.45 (dd, 1H), 7.11-7.06 (m, 3H), 7.03-6.99 (m, 2H), 6.98-6.95 (m, 2H), 5.40 (d, 1H), 4.29 (s, 2H), 3.81 (t, 1H), 3.64-3.46 (m, 5H), 3.35-3.26 (m, 4H), 1.88-1.83 (m, 1H), 0.94-0.88 (m, 2H), 0.65-0.60 (m, 2H); LC-MS (ESI) m/z 548/550 (Chlorine) (MH⁺) & 570/572 (Chlorine) (MNa⁺).

Compound 22: ¹H NMR (400 MHz, CD₃OD) δ 7.46 (dd, 1H), 7.11-7.03 (m, 4H), 7.01 (dd, 1H), 6.97-6.94 (m, 2H), 5.39 (d, 1H), 4.29 (s, 2H), 4.13 (q, 2H), 3.82 (t, 1H), 3.79 (s, 2H), 3.61 (dd, 1H), 3.57 (t, 1H), 3.56-3.52 (m, 1H), 3.37-3.28 (m, 2H), 1.88-1.82 (m, 1H), 1.23 (t, 3H), 0.93-0.88 (m, 2H), 0.64-0.60 (m, 2H); LC-MS (ESI) m/z 594/596 (Chlorine) (MNa⁺).

Compound 23: ¹H NMR (400 MHz, CD₃OD) δ 7.44 (dd, 1H), 7.11-7.00 (m, 5H), 6.97-6.94 (m, 2H), 5.41 (d, 1H), 4.29 (s, 2H), 4.00-3.56 (m, 3H), 3.82 (t, 1H), 3.58 (t, 1H), 3.36 (t, 1H), 2.81 (brs, 3H), 1.89-1.82 (m, 1H), 0.93-0.88 (m, 2H), 0.64-0.60 (m, 2H); LC-MS (ESI) m/z 516/518 (Chlorine) (MH⁺) & 538/540 (Chlorine) (MNa⁺).

Compound 24: ¹H NMR (400 MHz, CD₃OD) δ 7.44 (dd, 1H), 7.11-7.04 (m, 4H), 7.02 (dd, 1H), 6.98-6.94 (m, 2H), 5.42 (d, 1H), 4.29 (s, 2H), 4.00-3.57 (m, 3H), 3.83 (t, 1H), 3.59 (t, 1H), 3.40-3.30 (m, 2H), 3.36 (t, 1H), 1.88-1.82 (m, 1H), 0.99 (brs, 3H), 0.93-0.88 (m, 2H), 0.64-0.60 (m, 2H); LC-MS (ESI) m/z 530/532 (Chlorine) (MH⁺) & 552/554 (Chlorine) (MNa⁺).

Compound 25: ¹H NMR (400 MHz, CD₃OD) δ 7.45 (d, 1H), 7.11-7.05 (m, 4H), 7.01 (dd, 1H), 6.97-6.95 (m, 2H), 5.42 (d, 1H), 4.28 (s, 2H), 4.26-4.00 (m, 5H), 3.83 (t, 1H), 3.86-3.71 (m, 1H), 3.69-3.65 (m, 1H), 3.58 (t, 1H), 3.38 (t, 1H), 1.88-1.82 (m, 1H), 1.22 (t, 3H), 0.93-0.88 (m, 2H), 0.64-0.61 (m, 2H); LC-MS (ESI) m/z 588/590 (Chlorine) (MH⁺) & 610/612 (Chlorine) (MNa⁺).

Compound 26: ¹H NMR (400 MHz, CD₃OD) δ 7.47 (dd, 1H), 7.12-7.01 (m, 7H), 6.97-6.92 (m, 4H), 5.46 (d, 1H), 4.30 (s, 2H), 4.40-4.20 (m, 1H), 3.87 (t, 1H), 3.78 (ddd, 1H), 3.61 (t, 1H), 3.64-3.57 (m, 1H), 3.37 (t, 1H), 1.86-1.80 (m, 1H), 0.91-0.86 (m, 2H), 0.62-0.58 (m, 2H); LC-MS (ESI) m/z 612/614 (Chlorine) (MH⁺) & 634/636 (Chlorine) (MNa⁺).

Compound 27: ¹H NMR (300 MHz, CD₃OD) δ 7.43 (dd, 1H), 7.11-6.94 (m, 7H), 5.42 (d, 1H), 4.28 (s, 2H), 4.00-3.54 (m, 3H), 3.82 (t, 1H), 3.55 (t, 1H), 3.37-3.30 (m, 1H), 3.33 (s, 3H), 3.20 (brs, 4H), 1.90-1.84 (m, 1H), 1.59 (brs, 2H), 0.93-0.86 (m, 2H), 0.67-0.61 (m, 2H); LC-MS (ESI) m/z 596/598 (Chlorine) (MNa⁺).

Compound 28: ¹H NMR (400 MHz, CD₃OD) δ 7.44 (d, 1H), 7.10-6.94 (m, 7H), 5.38 (d, 1H), 4.28 (s, 2H), 3.81 (t, 1H), 3.79-3.73 (m, 1H), 3.54 (t, 1H), 3.45 (s, 3H), 3.41 (dd, 1H), 3.34-3.27 (m, 1H), 2.86 (dd, 1H), 1.86-1.82 (m, 1H), 0.92-0.87 (m, 2H), 0.64-0.60 (m, 2H); LC-MS (ESI) m/z 473/475 (Chlorine) (MH⁺) & 495/497 (Chlorine) (MNa⁺).

Compound 29: ¹H NMR (400 MHz, CD₃OD) δ 7.45 (d, 1H), 7.10-7.03 (m, 3H), 7.01-6.94 (m, 4H), 6.89 (d, 1H), 5.45 (d, 1H), 4.28 (s, 2H), 4.03 (dd, 1H), 3.84 (t, 1H), 3.65-3.53 (m, 4H), 3.15 (t, 2H), 1.86-1.81 (m, 1H), 0.92-0.88 (m, 2H), 0.64-0.60 (m, 2H); LC-MS (ESI) m/z 500/502 (Chlorine) (MH⁺).

Compound 30: ¹H NMR (400 MHz, CD₃OD) δ 7.47 (d, 1H), 7.37 (dd, 1H), 7.31 (d, 1H), 7.29-7.21 (m, 4H), 7.15-7.11 (m, 3H), 6.98 (td, 1H), 5.48 (d, 1H), 4.10 (dd, 1H), 4.07 (s, 2H), 3.92 (t, 1H), 3.61 (t, 1H), 3.55 (t, 1H); LC-MS (ESI) m/z 383 (MH⁺) & 405 (MNa⁺).

Compound 31: ¹H NMR (300 MHz, CD₃OD) δ 7.46 (d, 1H), 7.38 (d, 1H), 7.31 (d, 1H), 7.16-7.10 (m, 4H), 7.02-6.93 (m, 3H), 5.47 (d, 1H), 4.09 (dd, 1H), 4.01 (s, 2H), 3.92 (t, 1H), 3.64-3.52 (m, 2H), 1.89-1.80 (m, 1H), 0.93-0.86 (m, 2H), 0.64-0.58 (m, 2H); LC-MS (ESI) m/z 423 (MH⁺).

Compound 32: ¹H NMR (400 MHz, CD₃OD) δ 7.44 (d, 1H), 7.10-7.06 (m, 3H), 7.02-6.94 (m, 4H), 5.38 (d, 1H), 4.28 (s, 2H), 3.81 (t, 1H), 3.80-3.75 (m, 1H), 3.68-3.62 (m, 2H), 3.55 (t, 1H), 3.39 (dd, 1H), 3.32-3.29 (m, 1H), 2.87 (dd, 1H), 1.88-1.81 (m, 1H), 1.09 (t, 3H), 0.92-0.88 (m, 2H), 0.64-0.60 (m, 2H); LC-MS (ESI) m/z 487/489 (Chlorine) (MH$^+$) & 509/511 (Chlorine) (MNa$^+$).

Compound 34: $^1$H NMR (400 MHz, CD$_3$OD) δ 7.45 (d, 1H), 7.39 (d, 1H), 7.11-7.07 (m, 3H), 7.02-6.95 (m, 4H), 5.48 (d, 1H), 4.63 (d, 2H), 4.29 (s, 2H), 4.13 (dd, 1H), 3.85 (t, 1H), 3.60 (t, 1H), 3.54 (t, 1H), 2.83 (t, 1H), 1.88-1.82 (m, 1H), 0.93-0.88 (m, 2H), 0.65-0.61 (m, 2H); LC-MS (ESI) m/z 495/497 (Chlorine) (MH$^+$).

Compound 35: $^1$HNMR (400 MHz, CD$_3$OD) δ 7.45 (dd, 1H), 7.20 (d, 1H), 7.11-7.06 (m, 3H), 7.01-6.95 (m, 4H), 5.49 (d, 1H), 4.28 (s, 2H), 4.13 (dd, 1H), 3.85 (t, 1H), 3.74 (s, 3H), 3.64-3.57 (m, 2H), 1.89-1.82 (m, 1H), 0.93-0.88 (m, 2H), 0.65-0.61 (m, 2H); LC-MS (ESI) m/z 536/538 (Chlorine) (MNa$^+$).

Compound 36: $^1$H NMR (400 MHz, CD$_3$OD) δ 7.48 (d, 1H), 7.11-7.06 (m, 3H), 7.01-6.95 (m, 4H), 5.37 (d, 1H), 4.28 (s, 2H), 3.80 (t, 1H), 3.67 (ddd, 1H), 3.55-3.51 (m, 4H), 3.36 (t, 1H), 3.18 (dd, 1H), 2.94 (dd, 1H), 1.87-1.83 (m, 1H), 0.93-0.89 (m, 2H), 0.65-0.61 (m, 2H); LC-MS (ESI) m/z 538/540 (Chlorine) (MNa$^+$).

Compound 37: $^1$H NMR (400 MHz, CD$_3$OD) δ 7.46 (d, 1H), 7.38 (d, 1H), 7.32 (d, 1H), 7.16-7.09 (m, 4H), 7.02-6.93 (m, 3H), 5.48 (d, 1H), 4.10 (dd, 1H), 4.01 (s, 2H), 3.93 (t, 1H), 3.81 (s, 3H), 3.62 (t, 1H), 3.55 (t, 1H), 1.86-1.81 (m, 1H), 0.91-0.87 (m, 2H), 0.63-0.59 (m, 2H); LC-MS (ESI) m/z 437 (MH$^+$) & 459 (MNa$^+$).

Compound 38: $^1$H NMR (400 MHz, CD$_3$OD) δ 7.45 (d, 1H), 7.38 (d, 1H), 7.15-7.09 (m, 4H), 6.99 (ddd, 1H), 6.94-6.92 (m, 2H), 5.38 (d, 1H), 3.99 (s, 2H), 3.89 (t, 1H), 3.76 (ddd, 1H), 3.56 (t, 1H), 3.43 (s, 3H), 3.41 (dd, 1H), 3.34 (t, 1H), 2.84 (dd, 1H), 1.84-1.80 (m, 1H), 0.90-0.86 (m, 2H), 0.62-0.58 (m, 2H); LC-MS (ESI) m/z 439 (MH$^+$) & 461 (MNa$^+$).

Compound 39: $^1$H NMR (400 MHz, CD$_3$OD) δ 7.53 (d, 1H), 7.49 (dd, 1H), 7.42 (d, 1H), 7.15-7.11 (m, 4H), 7.06 (dd, 1H), 7.02-6.98 (m, 1H), 6.95-6.93 (m, 2H), 6.81 (dd, 1H), 5.44 (d, 1H), 4.01 (s, 2H), 3.93 (t, 1H), 3.75 (ddd, 1H), 3.58 (t, 1H), 3.43 (t, 1H), 3.42-3.30 (m, 1H), 3.04 (dd, 1H), 1.86-1.81 (m, 1H), 0.92-0.88 (m, 2H), 0.63-0.59 (m, 2H); LC-MS (ESI) m/z 556 (MNa$^+$).

Compound 40: $^1$H NMR (400 MHz, CD$_3$OD) δ 7.48 (d, 1H), 7.39 (d, 1H), 7.33 (d, 1H), 7.29-7.22 (m, 4H), 7.16-7.13 (m, 3H), 7.02-6.98 (m, 1H), 5.49 (d, 1H), 4.10 (dd, 1H), 4.08 (s, 2H), 3.93 (t, 1H), 3.82 (s, 3H), 3.62 (t, 1H), 3.55 (t, 1H); LC-MS (ESI) m/z 397 (MH$^+$) & 419 (MNa$^+$).

Compound 41: $^1$H NMR (400 MHz, CD$_3$OD) δ 7.46 (dd, 1H), 7.32 (d, 1H), 7.27-7.22 (m, 4H), 7.17-7.13 (m, 1H), 7.12-7.05 (m, 2H), 7.01 (dd, 1H), 5.49 (d, 1H), 4.35 (s, 2H), 4.10 (dd, 1H), 3.85 (t, 1H), 3.82 (s, 3H), 3.60 (t, 1H), 3.53 (t, 1H); LC-MS (ESI) m/z 453/455 (Chlorine) (MNa$^+$).

Compound 42: $^1$H NMR (400 MHz, CD$_3$OD) δ 7.47 (d, 1H), 7.39 (dt, 1H), 7.29-7.21 (m, 4H), 7.16-7.12 (m, 3H), 7.00 (ddd, 1H), 5.40 (d, 1H), 4.07 (s, 2H), 3.91 (t, 1H), 3.77 (ddd, 1H), 3.57 (t, 1H), 3.45 (s, 3H), 3.42 (dd, 1H), 3.37-3.30 (m, 1H), 2.86 (dd, 1H); LC-MS (ESI) m/z 399 (MH$^+$) & 421 (MNa$^+$).

Compound 43: $^1$H NMR (400 MHz, CD$_3$OD) δ 7.45 (dd, 1H), 7.26-7.21 (m, 4H), 7.17-7.13 (m, 1H), 7.11-7.06 (m, 2H), 7.01 (dd, 1H), 5.39 (d, 1H), 4.34 (s, 2H), 3.83 (t, 1H), 3.77 (ddd, 1H), 3.55 (t, 1H), 3.46 (s, 3H), 3.41 (dd, 1H), 3.35-3.30 (m, 1H), 2.87 (dd, 1H); LC-MS (ESI) m/z 433/435 (Chlorine) (MH$^+$) & 455/457 (Chlorine) (MNa$^+$).

Compound 44: $^1$H NMR (400 MHz, CD$_3$OD) δ 7.44 (dd, 1H), 7.20 (d, 1H), 7.11-7.06 (m, 3H), 7.02-6.95 (m, 4H), 5.49 (d, 1H), 4.28 (s, 2H), 4.14 (dd, 1H), 3.87 (t, 1H), 3.64-3.52 (m, 2H), 3.06 (s, 3H), 1.88-1.81 (m, 1H), 0.93-0.86 (m, 2H), 0.64-0.60 (m, 2H); LC-MS (ESI) m/z 529/531 (Chlorine) (MH$^+$) & 551/553 (Chlorine) (MNa$^+$).

Compound 45: $^1$H NMR (400 MHz, CD$_3$OD) δ 7.47 (d, 1H), 7.12-7.05 (m, 3H), 7.03-6.95 (m, 4H), 5.39 (d, 1H), 4.29 (s, 2H), 3.81 (t, 1H), 3.64 (ddd, 1H), 3.54 (t, 1H), 3.37-3.30 (m, 1H), 3.21 (dd, 1H), 2.85 (dd, 1H), 2.79 (s, 3H), 1.87-1.83 (m, 1H), 0.93-0.88 (m, 2H), 0.64-0.60 (m, 2H); LC-MS (ESI) m/z 531/533 (Chlorine) (MH$^+$) & 553/555 (Chlorine) (MNa$^+$).

Compound 46: $^1$H NMR (400 MHz, CD$_3$OD) δ 7.52-7.49 (m, 2H), 7.11-7.04 (m, 4H), 7.01-6.99 (m, 2H), 6.96-6.93 (m, 2H), 6.88 (dd, 1H), 5.41 (d, 1H), 4.27 (s, 2H), 3.84 (t, 1H), 3.74 (ddd, 1H), 3.55 (t, 1H), 3.40 (t, 1H), 3.33-3.30 (m, 1H), 3.04 (dd, 1H), 1.88-1.81 (m, 1H), 0.93-0.88 (m, 2H), 0.64-0.60 (m, 2H); LC-MS (ESI) m/z 590/592 (Chlorine) (MNa$^+$).

Compound 47: The ratio of the isomers ~1.2:1; LC-MS (ESI) m/z 486 (MNa$^+$).

Compound 48: $^1$H NMR (400 MHz, CD$_3$OD) δ 7.48 (d, 1H), 7.38 (d, 1H), 7.20-7.09 (m, 5H), 7.01-6.98 (m, 1H), 6.95-6.92 (m, 2H), 5.50 (d, 1H), 4.13 (dd, 1H), 3.99 (s, 2H), 3.94 (t, 1H), 3.72 (s, 3H), 3.67-3.60 (m, 2H), 1.86-1.79 (m, 1H), 0.91-0.86 (m, 2H), 0.62-0.58 (m, 2H).

Compound 49: $^1$H NMR (400 MHz, CD$_3$OD) δ 7.52 (d, 1H), 7.40 (d, 1H), 7.16-7.10 (m, 4H), 7.02-6.95 (m, 3H), 5.38 (d, 1H), 4.02 (s, 2H), 3.89 (t, 1H), 3.65 (ddd, 1H), 3.55 (t, 1H), 3.38 (t, 1H), 3.18 (dd, 1H), 2.94 (dd, 1H), 1.87-1.81 (m, 1H), 1.72 (s, 3H), 0.92-0.88 (m, 2H), 0.63-0.59 (m, 2H); LC-MS (ESI) m/z 488 (MNa$^+$).

Compound 50: $^1$H NMR (400 MHz, CD$_3$OD) δ 7.50 (d, 1H), 7.39 (d, 1H), 7.16-7.10 (m, 4H), 7.02-6.93 (m, 3H), 5.38 (d, 1H), 4.01 (s, 2H), 3.88 (t, 1H), 3.67 (ddd, 1H), 3.58-3.52 (m, 4H), 3.39 (t, 1H), 3.19 (dd, 1H), 2.95 (dd, 1H), 1.87-1.81 (m, 1H), 0.92-0.87 (m, 2H), 0.63-0.59 (m, 2H); LC-MS (ESI) m/z 504 (MNa$^+$).

Compound 51: $^1$H NMR (400 MHz, CD$_3$OD) δ 7.42 (dd, 1H), 7.11-7.05 (m, 3H), 7.04-6.95 (m, 4H), 6.19 (s, 1H), 5.40 (d, 1H), 4.28 (s, 2H), 3.85-3.80 (m, 2H), 3.64 (ddd, 1H), 3.56 (t, 1H), 3.38-3.28 (m, 2H), 1.89-1.82 (m, 1H), 0.93-0.88 (m, 2H), 0.65-0.61 (m, 2H); LC-MS (ESI) m/z 575/577 (Chlorine) (MNa$^+$).

Compound 52: The ratio of the isomers ~1.4:1; LC-MS (ESI) m/z 520/522 (Chlorine) (MNa$^+$).

Compound 53: $^1$H NMR (400 MHz, CD$_3$OD) δ 7.50 (d, 1H), 7.12-7.07 (m, 3H), 7.04-6.96 (m, 4H), 5.36 (d, 1H), 4.29 (s, 2H), 3.81 (t, 1H), 3.67-3.62 (m, 1H), 3.53 (t, 1H), 3.36 (t, 1H), 3.18 (dd, 1H), 2.94 (dd, 1H), 1.90-1.84 (m, 1H), 1.74 (s, 3H), 0.93-0.88 (m, 2H), 0.65-0.61 (m, 2H); LC-MS (ESI) m/z 522/524 (Chlorine) (MNa$^+$).

Compound 54: $^1$H NMR (300 MHz, CD$_3$OD) δ 7.50 (d, 1H), 7.41 (d, 1H), 7.18-7.09 (m, 4H), 7.04-6.93 (m, 3H), 5.41 (d, 1H), 4.01 (s, 2H), 3.90 (t, 1H), 3.67-3.54 (m, 2H), 3.39-3.30 (m, 1H), 3.21 (dd, 1H), 2.82 (dd, 1H), 2.74 (s, 3H), 1.88-1.79 (m, 1H), 0.92-0.86 (m, 2H), 0.63-0.58 (m, 2H); LC-MS (ESI) m/z 497 (MH$^+$) & 519 (MNa$^+$).

Compound 55: $^1$H NMR (300 MHz, CD$_3$OD) δ 7.43 (dd, 1H), 7.11-6.95 (m, 7H), 5.39 (d, 1H), 4.28 (s, 2H), 3.81 (t, 1H), 3.67-3.54 (m, 3H), 3.36-3.23 (m, 2H), 2.39 (sept, 1H), 1.89-1.82 (m, 1H), 1.06 (d, 3H), 1.05 (d, 3H), 0.94-0.88 (m, 2H), 0.65-0.60 (m, 2H); LC-MS (ESI) m/z 535/537 (Chlorine) (MNa$^+$).

Compound 56: $^1$H NMR (400 MHz, CD$_3$OD) δ 7.85 (dd, 2H), 7.61-7.45 (m, 5H), 7.10-6.94 (m, 7H), 5.54 (d, 1H), 4.28 (s, 2H), 4.26 (dd, 1H), 3.89 (t, 1H), 3.72-3.64 (m, 2H), 1.88-1.81 (m, 1H), 0.92-0.87 (m, 2H), 0.64-0.60 (m, 2H); LC-MS (ESI) m/z 582/584 (Chlorine) (MNa$^+$).

Compound 57: $^1$H NMR (400 MHz, CD$_3$OD) δ 7.45 (dd, 1H), 7.15 (d, 1H), 7.10-7.05 (m, 3H), 7.01-6.99 (m, 2H), 6.96-6.93 (m, 2H), 5.48 (d, 1H), 4.27 (s, 2H), 4.12 (dd, 1H), 3.86 (t, 1H), 3.65-3.58 (m, 2H), 1.86-1.82 (m, 1H), 1.47 (s, 9H), 0.92-0.87 (m, 2H), 0.64-0.60 (m, 2H); LC-MS (ESI) m/z 578/580 (Chlorine) (MNa+).

Compound 58: ¹H NMR (400 MHz, CD₃OD) δ 7.45 (dd, 1H), 7.19 (d, 1H), 7.09-7.05 (m, 3H), 7.01-6.99 (m, 2H), 6.96-6.94 (m, 2H), 5.49 (d, 1H), 4.27 (s, 2H), 4.20-4.11 (m, 3H), 3.86 (t, 1H), 3.65-3.58 (m, 2H), 1.86-1.80 (m, 1H), 1.25 (t, 3H), 0.92-0.87 (m, 2H), 0.63-0.60 (m, 2H); LC-MS (ESI) m/z 550/552 (Chlorine) (MNa+).

Compound 59: ¹H NMR (400 MHz, CD₃OD) δ 7.51 (dd, 1H), 7.42-7.38 (m, 3H), 7.23-7.19 (m, 2H), 7.08-7.04 (m, 3H), 7.01-6.98 (m, 2H), 6.94-6.92 (m, 2H), 5.42 (d, 1H), 4.27 (s, 2H), 3.85 (t, 1H), 3.76 (ddd, 1H), 3.56 (t, 1H), 3.41 (t, 1H), 3.36-3.30 (m, 1H), 3.05 (dd, 1H), 1.86-1.82 (m, 1H), 0.92-0.87 (m, 2H), 0.63-0.59 (m, 2H); LC-MS (ESI) m/z 584/586 (Chlorine) (MNa+).

Compound 60: ¹H NMR (400 MHz, CD₃OD) δ 7.49 (d, 1H), 7.11-7.06 (m, 3H), 7.01-6.99 (m, 2H), 6.97-6.94 (m, 2H), 5.37 (d, 1H), 4.28 (s, 2H), 3.82 (t, 1H), 3.65 (ddd, 1H), 3.54 (t, 1H), 3.37 (t, 1H), 3.16 (dd, 1H), 2.93 (dd, 1H), 1.88-1.81 (m, 1H), 1.37 (s, 9H), 0.92-0.88 (m, 2H), 0.64-0.60 (m, 2H); LC-MS (ESI) m/z 580/582 (Chlorine) (MNa+).

Compound 61: ¹H NMR (400 MHz, CD₃OD) δ 7.48 (d, 1H), 7.11-7.04 (m, 3H), 7.03-6.99 (m, 2H), 6.97-6.94 (m, 2H), 5.36 (d, 1H), 4.28 (s, 2H), 3.97-3.95 (m, 2H), 3.81 (t, 1H), 3.67 (ddd, 1H), 3.54 (t, 1H), 3.37 (t, 1H), 3.19 (dd, 1H), 2.95 (dd, 1H), 1.88-1.82 (m, 1H), 1.12 (t, 3H), 0.92-0.88 (m, 2H), 0.64-0.60 (m, 2H); LC-MS (ESI) m/z 552/554 (Chlorine) (MNa+).

Compound 62: ¹H NMR (400 MHz, CD₃OD) δ 7.46 (dd, 1H), 7.10-7.06 (m, 3H), 7.04-7.00 (m, 2H), 6.96-6.94 (m, 2H), 5.38 (d, 1H), 4.28 (s, 2H), 3.82 (t, 1H), 3.72 (dd, 1H), 3.64 (s, 3H), 3.62-3.54 (m, 2H), 3.37-3.30 (m, 2H), 3.25-3.23 (m, 2H), 1.88-1.82 (m, 1H), 0.92-0.87 (m, 2H), 0.64-0.60 (m, 2H); LC-MS (ESI) m/z 543/545 (Chlorine) (MH+) & 565/567 (Chlorine) (MNa+).

Compound 62': ¹H NMR (400 MHz, CD₃OD) δ 7.46 (dd, 1H), 7.12-6.95 (m, 7H), 5.39 (d, 1H), 4.28 (s, 2H), 3.82 (t, 1H), 3.74 (dd, 1H), 3.65-3.58 (m, 1H), 3.56 (t, 1H), 3.40-3.33 (m, 2H), 3.24 (s, 2H), 1.87-1.82 (m, 1H), 0.93-0.88 (m, 2H), 0.64-0.61 (m, 2H); LC-MS (ESI) m/z 529/531 (chlorine) (MH+) & 551/553 (chlorine) (MNa+).

Compound 63: ¹H NMR (400 MHz, CD₃OD) δ 7.47 (dd, 1H), 7.13-7.09 (m, 3H), 7.04-6.96 (m, 4H), 5.52 (d, 1H), 4.57 (d, 1H), 4.29 (s, 2H), 3.87 (t, 1H), 3.68 (dd, 1H), 3.53 (t, 1H), 1.88-1.84 (m, 1H), 0.93-0.88 (m, 2H), 0.65-0.61 (m, 2H); LC-MS (ESI) m/z 439/441 (Chlorine) (MH+) & 461/463 (Chlorine) (MNa+).

Compound 64: ¹H NMR (400 MHz, CD₃OD) δ 7.73-7.69 (m, 2H), 7.42-7.37 (m, 1H), 7.09-6.90 (m, 9H), 5.42 (d, 1H), 4.28, 4.25 (ABq, 2H), 3.87-3.81 (m, 5H), 3.70 (ddd, 1H), 3.60 (t, 1H), 3.54 (dd, 1H), 3.35-3.30 (m, 1H), 1.87-1.80 (m, 1H), 0.92-0.87 (m, 2H), 0.62-0.58 (m, 2H); LC-MS (ESI) m/z 577/579 (Chlorine) (MH+) & 599/601 (Chlorine) (MNa+).

Compound 65: ¹H NMR (400 MHz, CD₃OD) δ 9.24 (d, 1H), 7.50 (dd, 1H), 7.10-7.05 (m, 4H), 6.99 (dd, 1H), 6.96-6.93 (m, 2H), 5.64 (d, 1H), 4.90-4.88 (m, 1H), 4.27 (s, 2H), 4.01-3.94 (m, 2H), 3.72 (t, 1H), 1.86-1.82 (m, 1H), 0.92-0.87 (m, 2H), 0.64-0.60 (m, 2H); LC-MS (ESI) m/z 482/484 (Chlorine) (MH+) 504/506 (Chlorine) (MNa+).

Compound 66: ¹H NMR (300 MHz, CD₃OD) δ 8.16 (s, 1H), 7.27-7.08 (m, 6H), 7.02-6.96 (m, 3H), 5.39 (d, 1H), 4.89-4.85 (m, 1H), 4.64 (dd, 1H), 4.31 (s, 2H), 3.96 (dd, 1H), 3.78 (t, 1H), 3.57 (t, 1H), 3.36-3.28 (m, 1H); LC-MS (ESI) m/z 499/501 (Chlorine) (MH+) & 521/523 (Chlorine) (MNa+).

Compound 67: ¹H NMR (300 MHz, CD₃OD) δ 7.49 (dd, 1H), 7.34 (d, 1H), 7.30-7.23 (m, 4H), 7.20-7.01 (m, 4H), 5.50 (d, 1H), 4.37 (s, 2H), 4.12 (dd, 1H), 3.88 (t, 1H), 3.62 (t, 1H), 3.56 (t, 1H); LC-MS (ESI) m/z 417/419 (Chlorine) (MH+).

Example 2

Synthesis of Compounds 68-99

Compounds 68-99 were prepared according to a general synthetic method illustrated below using Compound 71 as an example.

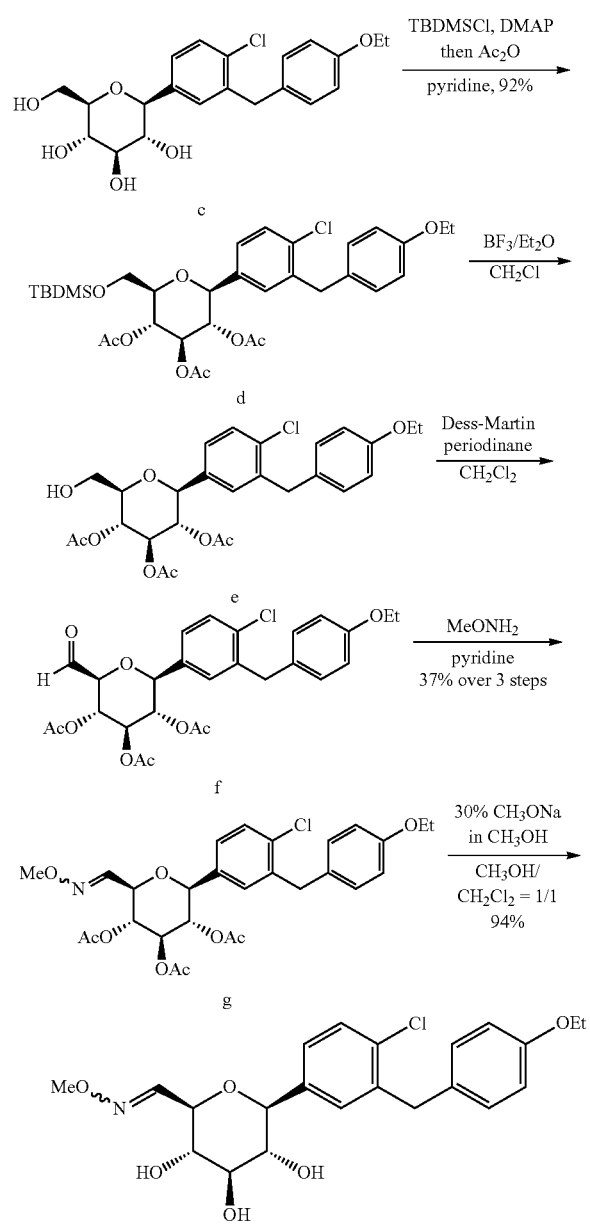

Compound c, the starting material shown in the scheme above, was prepared following the procedure described in J. Med. Chem. 2008, 51, 1145-1149.

Step 1. Synthesis of Compound d

To a stirred solution of Compound c (639.4 mg, 1.6 mmol) in pyridine (1.6 mL) was added DMAP (87.7 mg, 0.8 mmol) at room temperature. The reaction flask was cooled in an ice bath; a solution of TBDMSCl (353.6 mg, 2.4 mmol) in pyridine (1.6 mL) was added. The reaction was gradually warmed up to room temperature and stirred overnight. After the reaction was complete, $Ac_2O$ (1.5 mL, 15.6 mmol) was added. The obtained mixture was stirred at room temperature for another 3 h. The reaction flask was cooled in an ice bath, and $H_2O$ was added to quench the reaction. The mixture was extracted with $CH_2Cl_2$ and the organic phase was sequentially washed with 1 N HCl, $H_2O$, and saturated $NaHCO_3$ (aq). The organic phase was dried over $MgSO_4$, filtered, and concentrated under reduced pressure. The residue was purified by column chromatography (EtOAc/Hexane=1/10) to give Compound d (926.8 mg, 92%).

Step 2. Synthesis of Compound e

To a stirred solution of Compound d (926.8 mg, 1.43 mmol) in $CH_2Cl_2$ (7.0 mL) was added $BF_3.Et_2O$ (0.5 mL, 3.9 mmol) at 0° C. under argon. After stirring at 0° C. for 30 min, the reaction was quenched by the addition of saturated $NaHCO_3$ (aq). The mixture was extracted with $CH_2Cl_2$ and the organic phase was dried over $MgSO_4$, filtered, and concentrated under reduced pressure. The residue (crude Compound e) was used for next step without further purification.

Step 3. Synthesis of Compound f

To a stirred solution of crude Compound e (~1.4 mmol) in $CH_2Cl_2$ (5.6 mL) was added Dess-Martin periodinane (891 mg, 2.1 mmol) at room temperature under argon. After 3 h, the reaction was diluted with $CH_2Cl_2$, and saturated $NaHCO_3$ (aq) and saturated $Na_2S_2O_3$(aq) were added. The mixture was stirred for another 30 min, and then extracted with EtOAc. The organic phase was dried over $MgSO_4$, filtered, and concentrated under reduced pressure. The residue (crude Compound f) was used for next step without further purification.

Step 4. Synthesis of Compound g

To a stirred solution of aldehyde (crude Compound f, ~1.8 mmol) in pyridine (5.4 ml) was added O-methylhydroxylamine (227.6 mg, 2.7 mmol) at room temperature. After 2 h, the solvent was removed under reduced pressure. Water was added to the residue, and the mixture was extracted with $CH_2Cl_2$. The organic phase was dried over $MgSO_4$, filtered, and concentrated under reduced pressure. The residue was purified by column chromatography (EtOAc/Hexane=1/3) to provide Compound g (377.3 mg, 37% over 3 steps, cis-/trans-isomers).

Step 5. Synthesis of Compound 71

To a stirred solution of Compound g (377.3 mg, 0.7 mmol) in mixed solvents ($CH_3OH/CH_2Cl_2$, v/v:1/1, 6.8 mL) was added a 30% solution of $CH_3ONa$ in $CH_3OH$ (0.14 mL, 0.8 mmol) in an ice bath under argon. The reaction was warmed up to room temperature and stirred for 1-2 h. The reaction solution was neutralized with Amberlite-120 acidic resin, and the mixture was filtered to remove the resin followed by washings with methanol. The filtrate was concentrated under reduced pressure and the residue was purified by column chromatography ($CH_3OH/CH_2Cl_2$=1/30) to provide Compound 71 (276 mg, 94%, cis-/trans-isomers).

Compound 71: $^1$H NMR (400 MHz, $CD_3OD$, major isomer) δ 7.34 (d, 1H), 7.33 (d, 1H), 7.26-7.21 (m, 2H), 7.09-7.06 (m, 2H), 6.81-6.77 (m, 2H), 4.13 (d, 1H), 4.05-3.86 (m, 5H), 3.82 (s, 3H), 3.49-3.44 (m, 2H), 3.33-3.28 (m, 1H), 1.35 (t, 3H); LC-MS (ESI) m/z 436/438 (chlorine) (MH$^+$) & 458/460 (chlorine) (MNa$^+$).

Compounds 68-70 and 72-99 were prepared in a manner similar to that described immediately above and in Scheme 2. Of note, except Compounds 93 and 99, oximes or hydrazones were isolated as a mixture of cis/trans-isomers. The NMR assignments of these compounds were based on the characters of major isomers.

Compound 68: $^1$H NMR (300 MHz, $CD_3OD$) δ 7.34 (d, 1H), 7.33 (d, 1H), 7.26-7.20 (m, 2H), 7.10-7.05 (m, 2H), 6.81-6.77 (m, 2H), 4.13 (d, 1H), 4.08 (q, 2H), 4.01-3.86 (m, 5H), 3.50-3.43 (m, 2H), 3.42-3.28 (m, 1H), 1.35 (t, 3H), 1.21 (t, 3H); LC-MS (ESI) m/z 450/452 (chlorine) (MH$^+$) & 472/474 (chlorine) (MNa$^+$).

Compound 69: $^1$H NMR (400 MHz, $CD_3OD$) δ 7.42 (d, 1H), 7.35-7.20 (m, 8H), 7.09-7.06 (m, 2H), 6.80-6.75 (m, 2H), 5.06 (s, 2H), 4.13 (d, 1H), 4.04-3.88 (m, 5H), 3.48-3.46 (m, 2H), 3.34-3.31 (m, 1H), 1.34 (t, 3H); LC-MS (ESI) m/z 534/536 (chlorine) (MNa$^+$).

Compound 70: $^1$H NMR (400 MHz, $CD_3OD$) δ 7.34 (d, 1H), 7.33 (d, 1H), 7.26-7.21 (m, 2H), 7.10-7.06 (m, 2H), 6.81-6.77 (m, 2H), 4.13 (d, 1H), 4.05-3.87 (m, 5H), 3.50-3.46 (m, 2H), 3.34-3.30 (m, 1H), 1.35 (t, 3H); LC-MS (ESI) m/z 422/424 (chlorine) (MH$^+$) & 444/446 (chlorine) (MNa$^+$).

Compound 72: $^1$H NMR (400 MHz, $CD_3OD$) δ 7.37 (d, 1H), 7.34 (d, 1H), 7.26-7.21 (m, 2H), 7.09-7.06 (m, 2H), 6.81-6.77 (m, 2H), 4.19-4.12 (m, 3H), 4.05-3.88 (m, 5H), 3.62-3.59 (m, 2H), 3.48-3.46 (m, 2H), 3.33-3.29 (m, 4H), 1.35 (t, 3H); LC-MS (ESI) m/z 480/482 (chlorine) (MH$^+$) & 502/504 (chlorine) (MNa$^+$).

Compound 73: $^1$H NMR (400 MHz, $CD_3OD$) δ 7.37 (d, 1H), 7.34 (d, 1H), 7.26-7.21 (m, 2H), 7.09-7.07 (m, 2H), 6.80-6.78 (m, 2H), 4.59 (t, 2H), 4.14 (d, 1H), 4.05-3.89 (m, 5H), 3.50-3.44 (m, 2H), 3.34-3.27 (m, 1H), 2.17 (qt, 2H), 1.35 (t, 3H), 1.09 (t, 3H); LC-MS (ESI) m/z 510/512 (chlorine) (MNa$^+$).

Compound 74: $^1$H NMR (400 MHz, $CD_3OD$) δ 7.35 (d, 1H), 7.34 (d, 1H), 7.26-7.21 (m, 2H), 7.10-1.06 (m, 2H), 6.81-6.77 (m, 2H), 4.13 (d, 1H), 4.05-3.95 (m, 4H), 3.91-3.83 (m, 3H), 3.50-3.44 (m, 2H), 3.34-3.28 (m, 1H), 1.35 (t, 3H), 1.15-1.06 (m, 1H), 0.53-0.48 (m, 2H), 0.26-0.22 (m, 2H); LC-MS (ESI) m/z 476/478 (chlorine) (MH$^+$) & 498/500 (chlorine) (MNa$^+$).

Compound 75: $^1$H NMR (400 MHz, $CD_3OD$) δ 7.39 (d, 1H), 7.34 (d, 1H), 7.26-7.21 (m, 2H), 7.09-7.06 (m, 2H), 6.81-6.77 (m, 2H), 4.15-4.09 (m, 3H), 4.05-3.88 (m, 5H), 3.74-3.71 (m, 2H), 3.51-3.44 (m, 2H), 3.34-3.28 (m, 1H), 1.35 (t, 3H); LC-MS (ESI) m/z 466/468 (chlorine) (MH$^+$) & 488/490 (chlorine) (MNa$^+$).

Compound 76: $^1$H NMR (400 MHz, $CD_3OD$) δ 7.33 (d, 1H), 7.32 (d, 1H), 7.26-7.21 (m, 2H), 7.09-7.05 (m, 2H), 6.80-6.76 (m, 2H), 4.15-4.08 (m, 3H), 4.05-3.87 (m, 5H), 3.50-3.44 (m, 2H), 3.34-3.28 (m, 1H), 1.55 (t, 2H), 1.34 (t, 3H), 0.92 (s, 9H); LC-MS (ESI) m/z 506/508 (chlorine) (MH$^+$) & 528/530 (chlorine) (MNa$^+$).

Compound 77: $^1$H NMR (400 MHz, $CD_3OD$) δ 7.39 (d, 1H), 7.34 (d, 1H), 7.26-7.21 (m, 2H), 7.10-7.06 (m, 2H), 6.81-6.76 (m, 2H), 4.63 (d, 2H), 4.14 (d, 1H), 4.06-3.90 (m, 5H), 3.49-3.46 (m, 2H), 3.34-3.29 (m, 1H), 2.84 (t, 1H), 1.35 (t, 3H); LC-MS (ESI) m/z 460/462 (chlorine) (MH$^+$) & 482/484 (chlorine) (MNa$^+$).

Compound 78: $^1$H NMR (400 MHz, $CD_3OD$) δ 7.33 (d, 1H), 7.26-7.20 (m, 2H), 7.09-7.05 (m, 2H), 6.94 (d, 1H), 6.80-6.77 (m, 2H), 4.12 (d, 1H), 4.05-3.95 (m, 4H), 3.85-3.81 (m, 1H), 3.65 (t, 2H), 3.52-3.45 (m, 2H), 3.34-3.27 (m, 1H), 3.17 (t, 2H), 1.35 (t, 3H); LC-MS (ESI) m/z 465/467 (chlorine) (MH$^+$) & 487/489 (chlorine) (MNa$^+$).

Compound 79: $^1$H NMR (400 MHz, $CD_3OD$) δ 7.34 (d, 1H), 7.25-7.21 (m, 2H), 7.10-7.06 (m, 2H), 6.81-6.77 (m, 2H), 4.06 (d, 1H), 4.05-3.95 (m, 4H), 3.55 (ddd, 1H), 3.45 (s, 3H), 3.42 (t, 1H), 3.38 (dd, 1H), 3.26 (t, 1H), 3.25 (t, 1H), 2.87 (dd, 1H), 1.35 (t, 3H); LC-MS (ESI) m/z 460/462 (chlorine) (MNa$^+$).

Compound 80: ¹H NMR (400 MHz, CD₃OD) δ 7.33 (d, 1H), 7.25-7.20 (m, 3H), 7.08-7.05 (m, 2H), 6.80-6.77 (m, 2H), 4.15 (d, 1H), 4.05-3.91 (m, 5H), 3.74 (s, 3H), 3.55-3.47 (m, 2H), 3.35-3.30 (m, 1H), 1.34 (t, 3H); LC-MS (ESI) m/z 479/481 (chlorine) (MH⁺) & 501/503 (chlorine) (MNa⁺).

Compound 81: ¹H NMR (400 MHz, CD₃OD) δ 7.81-7.60 (m, 3H), 7.36-7.15 (m, 4H), 7.07 (d, 2H), 6.78 (d, 2H), 4.19 (d, 1H), 4.06-3.93 (m, 5H), 3.61 (t, 1H), 3.53 (t, 1H), 3.36 (t, 1H), 1.34 (t, 3H); LC-MS (ESI) m/z 531/533 (chlorine) (MH⁺) & 553/555 (chlorine) (MNa⁺).

Compound 82: The ratio of the isomers ~1.4:1; LC-MS (ESI) m/z 463/465 (chlorine) (MH⁺).

Compound 83: ¹H NMR (400 MHz, CD₃OD) δ 7.72 (d, 1H), 7.63 (d, 1H), 7.34 (d, 1H), 7.26-7.22 (m, 3H), 7.08-7.05 (m, 2H), 6.79-6.76 (m, 2H), 6.62 (dd, 1H), 4.19 (d, 1H), 4.06-3.93 (m, 5H), 3.61 (t, 1H), 3.53 (t, 1H), 3.36 (t, 1H), 1.33 (t, 3H); LC-MS (ESI) m/z 515/517 (chlorine) (MH⁺) & 537/539 (chlorine) (MNa⁺).

Compound 84: ¹H NMR (400 MHz, CD₃OD) δ 7.50 (dd, 1H), 7.31 (d, 1H), 7.27-7.22 (m, 2H), 7.10-7.06 (m, 2H), 6.99 (dd, 1H), 6.80-6.76 (m, 2H), 6.50 (dd, 1H), 4.09 (d, 1H), 4.05-3.93 (m, 4H), 3.54 (ddd, 1H), 3.43 (t, 1H), 3.37-3.27 (m, 3H), 3.02 (dd, 1H), 1.33 (t, 3H); LC-MS (ESI) m/z 517/519 (chlorine) (MH⁺) & 539/541 (chlorine) (MNa⁺).

Compound 85: ¹H NMR (400 MHz, CD₃OD) δ 7.34 (d, 1H), 7.26-7.22 (m, 2H), 7.10-7.06 (m, 2H), 6.81-6.77 (m, 2H), 4.08 (d, 1H), 4.06-3.95 (m, 4H), 3.62 (ddd, 1H), 3.44 (t, 1H), 3.41-3.24 (m, 3H), 2.91 (dd, 1H), 1.35 (t, 3H); LC-MS (ESI) m/z 424/426 (chlorine) (MH⁺) & 446/448 (chlorine) (MNa⁺).

Compound 86: ¹H NMR (400 MHz, CD₃OD) δ 7.60 (d, 1H), 7.42 (d, 1H), 7.36-7.22 (m, 5H), 7.11-7.03 (m, 3H), 6.77-6.73 (m, 2H), 4.19 (d, 1H), 4.02-3.89 (m, 5H), 3.59 (t, 1H), 3.54 (t, 1H), 3.37 (t, 1H), 1.31 (t, 3H); LC-MS (ESI) m/z 554/556 (chlorine) (MH⁺) & 576/578 (chlorine) (MNa⁺).

Compound 87: ¹H NMR (400 MHz, CD₃OD) δ 7.35 (d, 1H), 7.25-7.21 (m, 3H), 7.09-7.06 (m, 2H), 6.81-6.77 (m, 2H), 4.15 (d, 1H), 4.06-3.91 (m, 5H), 3.55-3.46 (m, 2H), 3.34 (t, 1H), 3.06 (s, 3H), 1.35 (t, 3H); LC-MS (ESI) m/z 494/496 (chlorine) (MH⁺) & 516/518 (chlorine) (MNa⁺).

Compound 88: ¹H NMR (400 MHz, CD₃OD) δ 8.09 (dd, 1H), 7.81 (dd, 1H), 7.49 (ddd, 1H), 7.44 (m, 1H), 7.33 (d, 1H), 7.29-7.23 (m, 2H), 7.07-7.03 (m, 2H), 6.82 (ddd, 1H), 6.77-6.73 (m, 2H), 4.20 (d, 1H), 4.06-3.90 (m, 5H), 3.61 (t, 1H), 3.53 (t, 1H), 3.37 (t, 1H), 1.32 (t, 3H); LC-MS (ESI) m/z 564/566 (chlorine) (MNa⁺).

Compound 89: ¹H NMR (400 MHz, CD₃OD) δ 8.07 (d, 2H), 7.33 (d, 1H), 7.28-7.20 (m, 3H), 7.07-7.02 (m, 4H), 6.78-6.75 (m, 2H), 4.19 (d, 1H), 4.04-3.92 (m, 5H), 3.58 (t, 1H), 3.53 (t, 1H), 3.37 (t, 1H), 1.32 (t, 3H); LC-MS (ESI) m/z 542/544 (chlorine) (MH⁺) & 564/566 (chlorine) (MNa⁺).

Compound 90: ¹H NMR (400 MHz, CD₃OD) δ 7.91 (d, 2H), 7.31 (d, 1H), 7.19-7.14 (m, 2H), 7.09-7.06 (m, 2H), 6.80-6.74 (m, 4H), 4.00-3.92 (m, 5H), 3.50 (ddd, 1H), 3.41 (t, 1H), 3.38-3.23 (m, 3H), 2.95 (dd, 1H), 1.33 (t, 3H); LC-MS (ESI) m/z 544/546 (chlorine) (MH⁺) & 566/568 (chlorine) (MNa⁺).

Compound 91: ¹H NMR (400 MHz, CD₃OD) δ 8.73-8.70 (m, 2H), 7.84-7.80 (m, 2H), 7.67 (d, 1H), 7.35 (d, 1H), 7.27-7.23 (m, 2H), 7.10-7.06 (m, 2H), 6.81-6.78 (m, 2H), 4.20 (d, 1H), 4.08-3.94 (m, 5H), 3.62 (t, 1H), 3.53 (t, 1H), 3.67 (t, 1H), 1.34 (t, 3H); LC-MS (ESI) m/z 526/527 (chlorine) (MH⁺) & 548/550 (chlorine) (MNa⁺).

Compound 92: ¹H NMR (400 MHz, CD₃OD) δ 7.39 (d, 1H), 7.35 (d, 1H), 7.25-7.21 (m, 2H), 7.09-7.05 (m, 2H), 6.80-6.76 (m, 2H), 4.16 (d, 1H), 4.05-3.94 (m, 5H), 3.69 (s, 4H), 3.56 (t, 1H), 3.50 (t, 1H), 3.36 (dd, 1H), 1.34 (s, 3H); LC-MS (ESI) m/z 489/491 (chlorine) (MH⁺) & 511/513 (chlorine) (MNa⁺).

Compound 93: ¹H NMR (400 MHz, DMSO) δ 11.68 (s, 1H), 7.84 (d, 2H), 7.63 (d, 1H), 7.59-7.48 (m, 3H), 7.37 (d, 1H), 7.31 (s, 1H), 7.22 (d, 1H), 7.08 (d, 2H), 6.81 (d, 2H), 5.19-5.18 (m, 2H), 4.96 (d, 1H), 4.16 (d, 1H), 4.01-3.87 (m, 5H), 3.39-3.21 (m, 3H), 1.27 (t, 3H); LC-MS (ESI) m/z 525/527 (chlorine) (MH⁺) & 547/549 (chlorine) (MNa⁺).

Compound 94: ¹H NMR (400 MHz, DMSO) δ 11.59 (s, 0.5H), 11.52 (s, 0.5H), 7.82-7.24 (m, 5H), 7.07 (d, 2H), 6.87-6.78 (m, 3H), 5.22 (brs, 2H), 4.99 (s, 1H), 4.16 (d, 1H), 4.01-3.89 (m, 5H), 3.36-3.23 (m, 3H), 2.45 (s, 3H), 1.28 (t, 3H); LC-MS (ESI) m/z 567/569 (chlorine) (MNa⁺).

Compound 95: ¹H NMR (400 MHz, DMSO) δ 11.79 (s, 1H), 7.82-7.17 (m, 6H), 7.07 (d, 2H), 6.80-6.78 (m, 2H), 5.30-5.19 (m, 2H), 4.99 (d, 1H), 4.19 (d, 1H), 4.01-3.91 (m, 5H), 3.36-3.20 (m, 3H), 1.27 (t, 3H); LC-MS (ESI) m/z 565/567 (chlorine) (MH⁺) & 587/589 (chlorine) (MNa⁺).

Compound 96: ¹H NMR (400 MHz, DMSO) δ 11.75 (s, 1H), 7.87 (d, 2H), 7.64 (d, 1H), 7.58 (d, 2H), 7.37 (d, 1H), 7.31 (d, 1H), 7.22 (dd, 1H), 7.08 (d, 2H), 6.83-6.79 (m, 2H), 5.20-5.19 (m, 2H), 4.97 (d, 1H), 4.16 (d, 1H), 4.01-3.88 (m, 5H), 3.39-3.34 (m, 2H), 3.27-3.22 (m, 1H), 1.27 (t, 3H); LC-MS (ESI) m/z 559/561 (chlorine) (MH⁺) & 581/583 (chlorine) (MNa⁺).

Compound 97: ¹H NMR (400 MHz, DMSO) δ 11.55 (s, 1H), 8.25 (s, 1H), 7.64-7.54 (m, 3H), 7.38 (d, 1H), 7.32 (d, 1H), 7.23 (dd, 1H), 7.08 (d, 2H), 6.81 (d, 2H), 5.22-5.20 (m, 2H), 4.99 (d, 1H), 4.18 (d, 1H), 4.02-3.89 (m, 5H), 3.40-3.36 (m, 2H), 3.29-3.23 (m, 1H), 1.27 (t, 3H); LC-MS (ESI) m/z 531/533 (chlorine) (MH⁺) & 553/555 (chlorine) (MNa⁺).

Compound 98: ¹H NMR (400 MHz, CD₃OD) δ 7.34 (d, 1H), 7.33 (d, 1H), 7.26-7.21 (m, 2H), 7.07-7.03 (m, 2H), 6.96-6.93 (m, 2H), 4.13 (d, 1H), 4.04, 4.00 (ABq, 2H), 3.92-3.87 (m, 1H), 3.51-3.45 (m, 2H), 3.34-3.29 (m, 1H), 1.86-1.80 (m, 1H), 0.92-0.87 (m, 2H), 0.63-0.59 (m, 2H); LC-MS (ESI) m/z 440/442 (chlorine) (MNa⁺).

Compound 99: ¹H NMR (400 MHz, DMSO) δ 7.35 (d, 1H), 7.29-7.15 (m, 8H), 7.09-7.05 (m, 2H), 6.82-6.79 (m, 2H), 6.75 (d, 1H), 5.03 (d, 1H), 4.89-4.86 (m, 2H), 4.12 (d, 2H), 4.03 (d, 1H), 4.00-3.92 (m, 4H), 3.67 (dd, 1H), 3.39-3.12 (m, 3H), 1.28 (t, 3H); LC-MS (ESI) m/z 511/513 (chlorine) (MH⁺) & 533/535 (chlorine) (MNa⁺).

Example 3

Synthesis of Compounds 100-110

The general procedure is illustrated immediately below using compound 105 as a specific example.

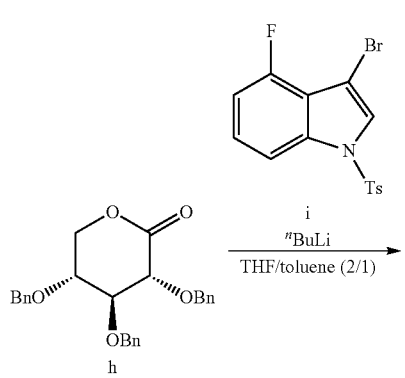

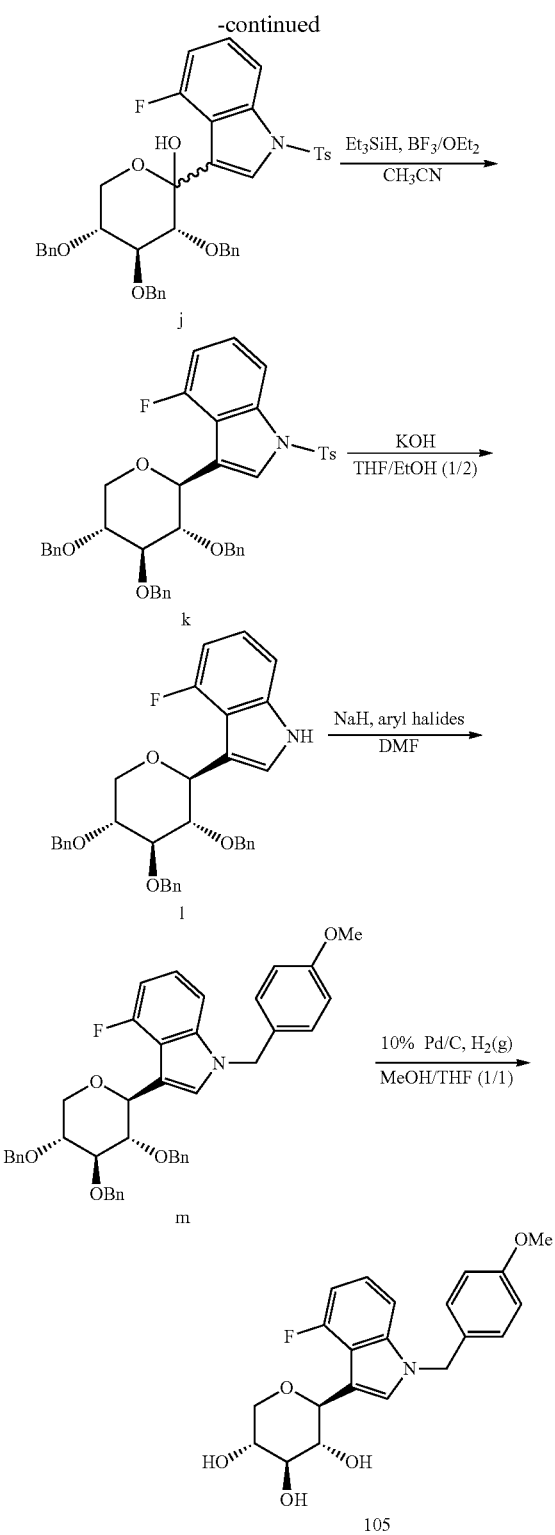

tion was poured into saturated aqueous ammonium chloride and the mixture was extracted with CH$_2$Cl$_2$. The organic layer was dried over MgSO$_4$, filtered, and concentrated under reduced pressure. The residue was purified by column chromatography (EtOAc/Hex=1/4) to give Compound j (550 mg, 72%).

Step 2. Synthesis of Compound k

Et$_3$SiH (0.60 mL, 3.89 mmol) and then BF$_3$.Et$_2$O (50 μL, 0.19 mmol) were added to a stirred solution of Compound j (550 mg, 0.78 mmol) in CH$_3$CN (10 mL) at 0° C. under argon and then the reaction was warmed to room temperature gradually. After 1 h, the reaction was quenched by the addition of saturated aqueous sodium bicarbonate at 0° C. and extracted with CH$_2$Cl$_2$. The organic layer was dried over MgSO$_4$, filtered and concentrated under reduced pressure. The residue was purified by column chromatography (EtOAc/Hex=1/4) to give Compound k (406 mg, 76%).

Step 3. Synthesis of Compound l 590 mg of KOH (10.58 mmol) was added to a stirred solution of Compound k (366 mg, 0.53 mmol) in THF/EtOH (v/v, 1/2, 18 mL) at room temperature. The reaction was warmed to 60° C. and heated for 20 h. The reaction was cooled to 0° C. and neutralized by the addition of 1 N HCl (aq). The mixture was extracted with EtOAc and the organic layer was dried over MgSO$_4$, filtered and concentrated under reduced pressure. The residue was purified by column chromatography (EtOAc/Hex=1/3) to afford the desired product Compound l (200 mg, 70%).

Step 4. Synthesis of Compound m

NaH (4.0 mg, 0.094 mmol) and 4-methoxybenzyl chloride (13 μL, 0.094 mmol) were sequentially added to a stirred solution of Compound l (42.5 mg, 0.079 mmol) in DMF (0.5 mL) at 0° C. The reaction was slowly warmed to room temperature and stirred for 16 h. The reaction was quenched by the addition of H$_2$O at 0° C. and extracted with CH$_2$Cl$_2$. The organic layer was dried over MgSO$_4$, filtered and concentrated under reduced pressure. The obtained residue was purified by column chromatography (EtOAc/Hexane=1/4 to 1/3) to afford the desired product Compound m (49.4 mg, 95%).

Step 5. Synthesis of Compound 105

A mixture of Compound m (49.4 mg, 0.075 mmol) and 10% Pd/C (100 mg) in MeOH/THF (v/v, 1/1, 4.0 mL) was stirred at room temperature under 1 atm H$_2$ (g) for 1.5 h. The reaction was filtered through a pad of Celite and the filtrate was concentrated under reduced pressure. The obtained residue was then purified by column chromatography (MeOH/CH$_2$Cl$_2$=1/20 to 1/10) to provide the final product Compound 105 (22.6 mg, 78%).

Compound 105: $^1$H NMR (300 MHz, CD$_3$OD) δ 7.34 (s, 1H), 7.16-7.01 (m, 4H), 6.85-6.80 (m, 2H), 6.75-6.69 (m, 1H), 5.27 (s, 2H), 4.51 (dd, 1H), 3.93 (dd, 1H), 3.79-3.73 (m, 1H), 3.73 (s, 3H), 3.64 (ddd, 1H), 3.43 (t, 1H), 3.36 (t, 1H); LC-MS (ESI) m/z 388 (MH$^+$) & 410 (MNa$^+$).

Compounds 101-104 and 106-110 were prepared in a manner similar to that described immediately above and in Scheme 3.

Compound 100: $^1$H NMR (400 MHz, CD$_3$OD) δ 7.71-7.69 (m, 1H), 7.34 (s, 1H), 7.30-7.17 (m, 6H), 7.11 (ddd, 1H), 7.04 (ddd, 1H), 5.36 (s, 2H), 4.42 (d, 1H), 3.98 (dd, 1H), 3.75 (t, 1H), 3.68 (ddd, 1H), 3.45 (t, 1H), 3.38 (dd, 1H); LC-MS (ESI) m/z 340 (MH$^+$) & 362 (MNa$^+$).

Compound 101: $^1$H NMR (400 MHz, CD$_3$OD) δ 7.69 (d, 1H), 7.33 (s, 1H), 7.28 (d, 1H), 7.21-7.17 (m, 2H), 7.12-7.08 (m, 1H), 7.05-6.97 (m, 3H), 5.34 (s, 2H), 4.41 (d, 1H), 3.97 (dd, 1H), 3.74 (t, 1H), 3.67 (ddd, 1H), 3.44 (t, 1H), 3.37 (t, 1H); LC-MS (ESI) m/z 358 (MH$^+$) & 380 (MNa$^+$).

Compound 102: $^1$H NMR (400 MHz, CD$_3$OD) δ 7.67 (d, 1H), 7.32-7.30 (m, 2H), 7.14-7.08 (m, 3H), 7.04-7.00 (m, 1H), 6.84-6.81 (m, 2H), 5.27 (s, 2H), 4.40 (d, 1H), 3.96 (dd, 1H), 3.75-3.71 (m, 1H), 3.73 (s, 3H), 3.67 (ddd, 1H), 3.44 (t, 1H), 3.37 (t, 1H); LC-MS (ESI) m/z 370 (MH$^+$) & 392 (MNa$^+$).

Compound 103: $^1$H NMR (400 MHz, CD$_3$OD) δ 7.68 (d, 1H), 7.32-7.30 (m, 4H), 7.12-7.08 (m, 3H), 7.04-7.01 (m, 1H), 5.31 (s, 2H), 4.41 (d, 1H), 3.96 (dd, 1H), 3.74 (dd, 1H), 3.67 (ddd, 1H), 3.44 (t, 1H), 3.37 (t, 1H), 1.26 (s, 9H); LC-MS (ESI) m/z 396 (MH$^+$) & 418 (MNa$^+$).

Compound 104: $^1$H NMR (300 MHz, CD$_3$OD) δ 7.80-7.70 (m, 4H), 7.61 (s, 1H), 7.45-7.39 (m, 3H), 7.35-7.30 (m, 2H), 7.12-7.01 (m, 2H), 5.51 (s, 2H), 4.43 (d, 1H), 3.98 (dd, 1H), 3.76 (t, 1H), 3.68 (ddd, 1H), 3.48-3.35 (m, 2H); LC-MS (ESI) m/z 390 (MH$^+$) & 412 (MNa$^+$).

Compound 106: $^1$H NMR (300 MHz, CD$_3$OD) δ 7.46 (d, 1H), 7.30 (s, 1H), 7.11 (d, 2H), 6.95 (td, 1H), 6.85-6.78 (m, 3H), 5.39 (s, 2H), 4.37 (d, 1H), 3.96 (dd, 1H), 3.73 (s, 3H), 3.73-3.61 (m, 2H), 3.45-3.32 (m, 2H); LC-MS (ESI) m/z 388 (MH$^+$) & 410 (MNa$^+$).

Compound 107: $^1$H NMR (400 MHz, CD$_3$OD) δ 7.67 (d, 1H), 7.30-7.28 (m, 2H), 7.11-6.96 (m, 6H), 5.28 (s, 2H), 4.40 (d, 1H), 3.96 (dd, 1H), 3.73 (t, 1H), 3.67 (ddd, 1H), 3.43 (t, 1H), 3.37 (t, 1H), 1.86-1.82 (m 1H), 0.93-0.88 (m, 2H), 0.62-0.58 (m, 2H); LC-MS (ESI) m/z 380 (MH$^+$) & 402 (MNa$^+$).

Compound 108: $^1$H NMR (400 MHz, CD$_3$OD) δ 7.46 (d, 1H), 7.30 (s, 1H), 7.05-6.92 (m, 5H), 6.83-6.78 (m, 1H), 5.41 (s, 2H), 4.37 (d, 1H), 3.96 (dd, 1H), 3.69-3.62 (m, 2H), 3.42 (t, 1H), 3.36 (t, 1H), 1.90-1.80 (m, 1H), 0.94-0.88 (m, 2H), 0.62-0.58 (m, 2H); LC-MS (ESI) m/z 398 (MH$^+$) & 420 (MNa$^+$).

Compound 109: $^1$H NMR (400 MHz, CD$_3$OD) δ 7.54 (d, 1H), 7.23 (s, 1H), 6.96-6.89 (m, 3H), 6.81-6.78 (m, 3H), 5.54 (s, 2H), 4.41 (d, 1H), 3.97 (dd, 1H), 3.75 (dd, 1H), 3.67 (ddd, 1H), 3.44 (t, 1H), 3.38 (t, 1H), 2.45 (s, 3H), 1.86-1.79 (m, 1H), 0.93-0.85 (m, 2H), 0.61-0.57 (m, 2H); LC-MS (ESI) m/z 394 (MH$^+$) & 416 (MNa$^+$).

Compound 110: $^1$H NMR (400 MHz, CD$_3$OD) δ 7.69-7.67 (m, 1H), 7.31-7.29 (m, 2H), 7.12-7.00 (m, 6H), 5.31 (s, 2H), 4.41 (d, 1H), 3.96 (dd, 1H), 3.74 (dd, 1H), 3.67 (ddd, 1H), 3.43 (t, 1H), 3.37 (t, 1H), 2.52 (t, 2H), 1.58 (sext, 2H), 0.89 (t, 3H); LC-MS (ESI) m/z 382 (MH$^+$) & 404 (MNa$^+$).

Example 4

SGLT2 Inhibition Assay

Stably transfected CHO-K1 cells were used for transport studies. Sodium-dependent D-glucose transport was determined by means of [$^{14}$C]-α-methyl-D-glucopyranoside ([$^{14}$C]AMG, specific radioactivity 300 mCi/mmol). For the purpose of this study, Krebs-Ringer-Henseleit sodium (KRH-Na) solution containing 120 mM NaCl, 4.7 mM KCl, 1.2 mM MgCl$_2$, 2.2 mM CaCl$_2$, 10 mM Hepes (pH 7.4 with Tris/HCl) was used to assess sodium-dependent D-glucose transport. Briefly, hSGLT2/CHO-K1 cells were seeded in white-walled 96-well plates at a density of 30,000 cells per well in growth medium. After 48 h of culture at 37° C. in a humidified atmosphere containing 5% CO$_2$, the culture medium of the 96-wells was taken off. Wells were washed twice with 200 μL KRH-Na solution and incubated in KRH-Na solution containing 3 uM [$^{14}$C]AMG in the absence or presence of inhibitors for up to 120 min at 37° C. At the end of the uptake period, the transport buffer was removed and the uptake of [$^{14}$C] AMG was stopped by adding ice-cold stop buffer (KRH-Na containing 0.5 mM phlorizin). The wells were rinsed three times with 100 μL stop buffer using the microplate washer (TEcan, Männedorf, Switzerland). After the third rinse, the stop buffer was completely removed from the wells and the cells were solubilized by adding 50 μL 1% sodium dodecyl sulfate. After 10 min at room temperature, the microtiter plate was added 100 μL scintillation cocktail and taken for scintillation counting of radioactive [$^{14}$C]AMG using a TopCount (Perkin Elmer). The percentage of inhibition of inhibitors was calculated by comparing count per minute (CPM) in inhibitor-containing wells with CPM in wells containing only DMSO vehicles. Phlorizin was evaluated in parallel in every assay. A dose-response curve was fitted to a sigmoidal dose-response model using GraphPad software to determine the inhibitor concentration at half-maximal response (EC$_{50}$).

Compounds 1-110 were tested in this assay. Unexpectedly, most of the test compounds have EC$_{50}$ values between 1 nM and 1 μM.

Example 5

In Vivo Urine Glucose Excretion Assay

Male Sprague-Dawley rats were used for glucosuria assessment. Male Sprague-Dawley rats of 8-10 weeks old were obtained from BioLasco, Ilan, Taiwan. The rats to be tested were fasted overnight and divided into 6 weight-matched groups. The rats were mildly anesthetized with a mixed gas of 30% O$_2$ and 70% CO$_2$ by inhalation and were orally gavaged with a single dose of the tested compounds (0.1, 1, 10, and 50 mg/kg), dapagliflozin (reference compound, 1 mg/kg), or vehicle. Each of the tested rats was subsequently dosed orally with 50% glucose solution (2 g/kg). The rats were returned to metabolism cages (ISHIHALA, Tokyo, Japan) for 24-hour urine collection and were re-fed at 1 h after the glucose challenge. Volume of the urine was measured and recorded. The urine samples were measured for glucose levels by a DRI-CHEM 3500 analyzer (FUJI, Tokyo, Japan). A P value of less than 0.05 was considered statistically significant.

Compounds 70, 71, 78, 79, 81, 87, 93, and 95 were found to exhibit strong effect in increasing urinary glucose excretion in a dose-dependent manner.

Example 6

In Vivo Anti-Hyperglycemia Assay

Streptozotocin-induced diabetes rats were used for assessment of blood glucose lowering effect. Adult male Sprague Dawley rats were obtained from BioLasco, Ilan, Taiwan. The rats received an intraperitoneal injection of streptozotocin (Sigma, Cat. No. S0130, St. Louis, Mo., USA) at a concentration of 65 mg/kg every other day. The streptozotocin solution was freshly prepared in 0.01 M citrate buffer. Blood samples were collected via tail vein with a 25 G needle once a week and were tested using a blood glucometer (ACCU-CHEK® from Roche, Basel, Schweiz) for glucose level. A glucose level of higher than 450 mg/dL indicates streptozotocin-induced diabetes. The diabetic rats were divided into 3-6 groups and were orally administered with a single dose of the tested compounds, dapagliflozin (reference compound), or vehicle. Blood samples were collected via tail vein at 0 (pre-dose), 0.5, 1, 2, 3, 4, and 5 hr after the oral administration and were measured for blood glucose levels with the glucometer. A P value of less than 0.05 was considered statistically significant.

Compounds 70, 78, 87, 93, 95, and 108 were found to exhibit strong anti-hyperglycemia effect at various dosages.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of formula (I):

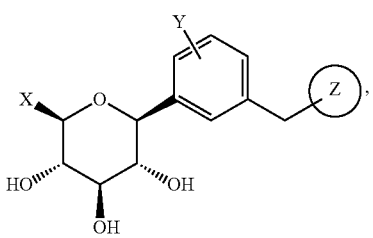

wherein
X is $R_1ONHCH_2$—, $R_1R_2NNHCH_2$—, $R_1ON=CH$—, $R_1HNC(S)NHCH_2$—, $R_1R_2NN=CH$—, $R_1HNC(S)NHN=CH$—, or $R_1C(O)NHN=CH$—, in which each of $R_1$ and $R_2$, independently, is H, halo, $C_1$-$C_{10}$ alkyl, $C_1$-$C_{10}$ alkoxyl, $C_2$-$C_{10}$ alkenyl, $C_2$-$C_{10}$ alkynyl, $C_3$-$C_{10}$ cycloalkyl, $C_3$-$C_{10}$ heterocycloalkyl, aryl, or heteroaryl;

Y is H, halo, amino, $C_1$-$C_{10}$ alkyl, or $C_1$-$C_{10}$ alkoxyl; and

Z is unsubstituted aryl or aryl substituted with halo, hydroxyl, amino, $C_1$-$C_{10}$ alkyl, $C_1$-$C_{10}$ alkoxyl, $C_3$-$C_{10}$ cycloalkyl, $C_3$-$C_{10}$ heterocycloalkyl, $C_2$-$C_{10}$ alkenyl, $C_2$-$C_{10}$ alkynyl, aryl, or heteroaryl.

2. The compound of claim 1, wherein Y is halo and Z is aryl substituted with $C_1$-$C_{10}$ alkoxyl or $C_3$-$C_{10}$ cycloalkyl.

3. The compound of claim 1, wherein the compound is one of the compounds as shown below:

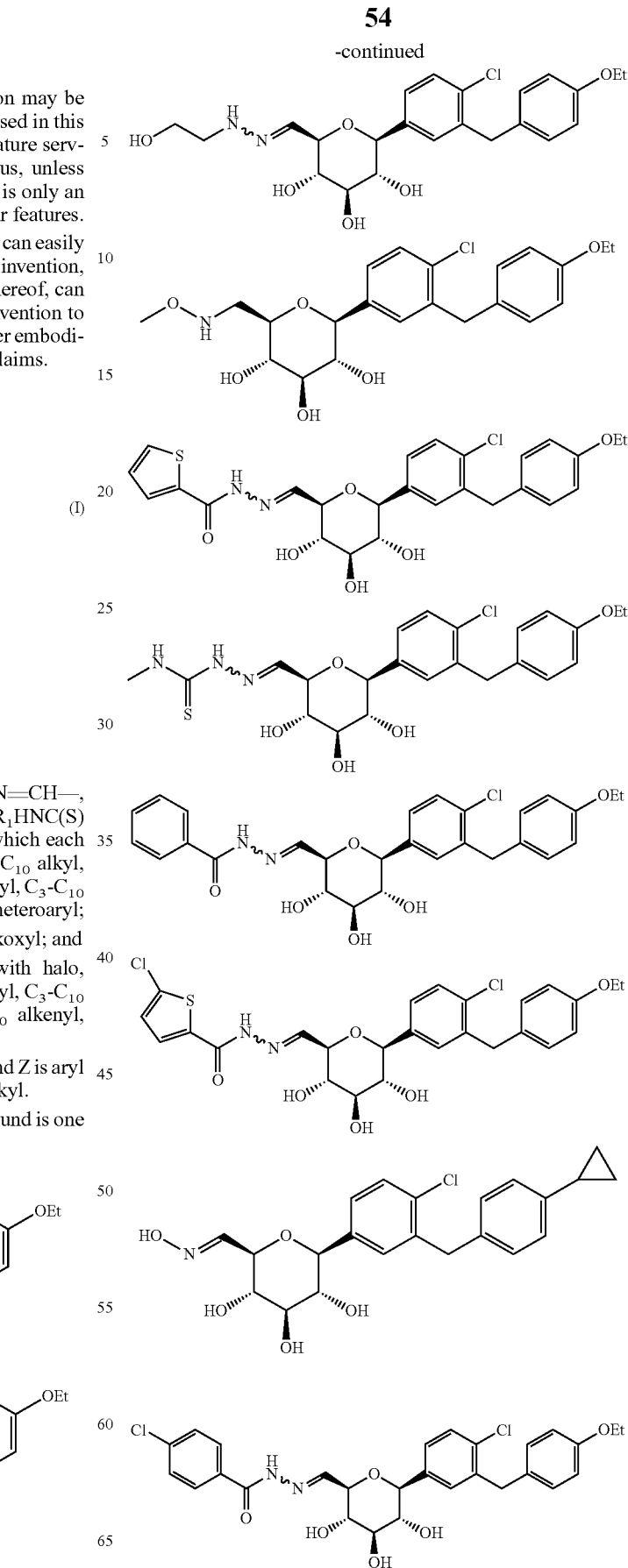

-continued

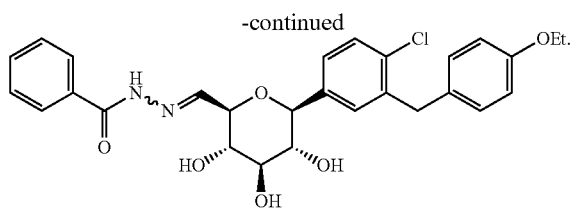

4. The compounds of claim 1, wherein the compound is one of the compounds as shown below:

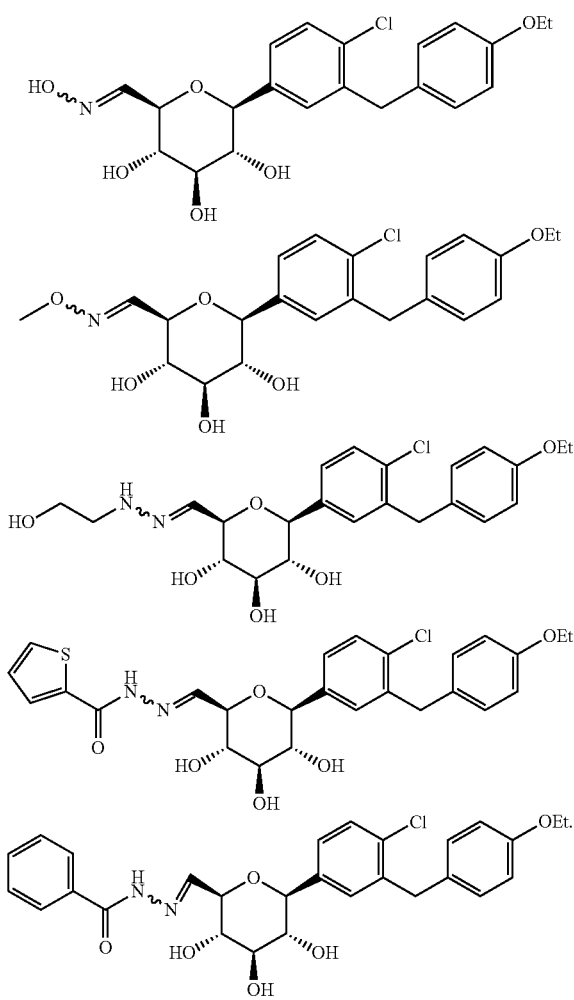

5. A compound of formula (II):

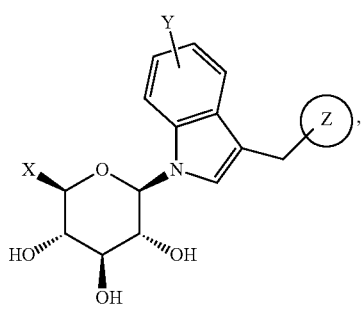

wherein

X is CN, heteroaryl, heteroaryl-CH$_2$—, N$_3$CH$_2$—, NH$_2$CH$_2$—, R$_1$C(O)NHNHCH$_2$—, R$_1$R$_2$NCH$_2$—, R$_1$C(O)NHCH$_2$—, R$_1$HNC(O)NHCH$_2$—, R$_1$HNC(S)NHCH$_2$—, R$_1$ONHCH$_2$—, R$_1$R$_2$NNHCH$_2$—, R$_{10}$—N=CH—, R$_1$R$_2$NN=CH—, or R$_1$C(O)NHN=CH—, in which each of R$_1$ and R$_2$, independently, is H, halo, C$_1$-C$_{10}$ alkyl, C$_1$-C$_{10}$ alkoxyl, C$_3$-C$_{10}$ cycloalkyl, C$_3$-C$_{10}$ heterocycloalkyl, C$_2$-C$_{10}$ alkenyl, C$_2$-C$_{10}$ alkynyl, aryl, or heteroaryl; or R$_1$ and R$_2$, together with the nitrogen atom to which they are attached, is heteroaryl;

Y is H, halo, amino, C$_1$-C$_{10}$ alkyl, or C$_1$-C$_{10}$ alkoxyl; and

Z is unsubstituted aryl or aryl substituted with halo, hydroxyl, amino, C$_1$-C$_{10}$ alkyl, C$_1$-C$_{10}$ alkoxyl, C$_3$-C$_{10}$ cycloalkyl, C$_3$-C$_{10}$ heterocycloalkyl, C$_2$-C$_{10}$ alkenyl, C$_2$-C$_{10}$ alkynyl, aryl, or heteroaryl.

6. The compound of claim 5, wherein X is R$_1$C(O)NHCH$_2$— or R$_1$C(O)NHNHCH$_2$—, Y is H or halo, and Z is aryl substituted with C$_3$-C$_{10}$ cycloalkyl.

7. The compound of claim 5, wherein the compound is one of the compounds as shown below:

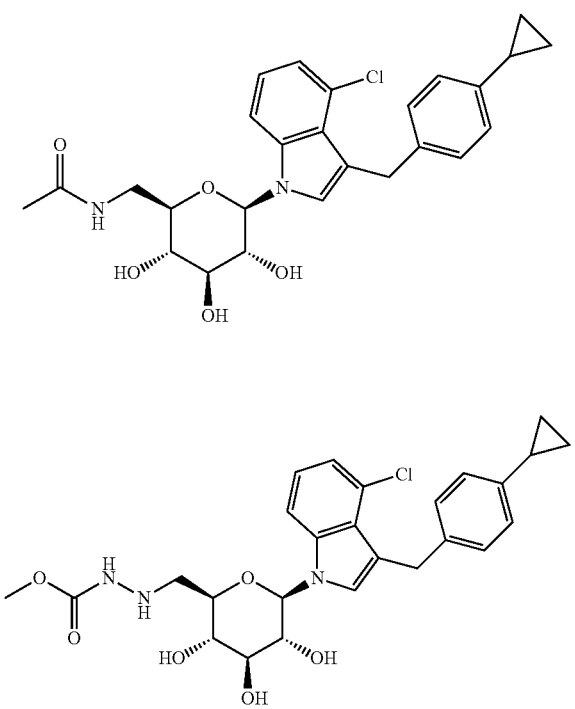

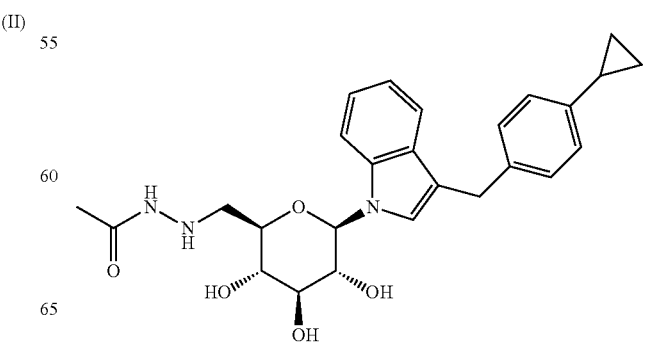

-continued

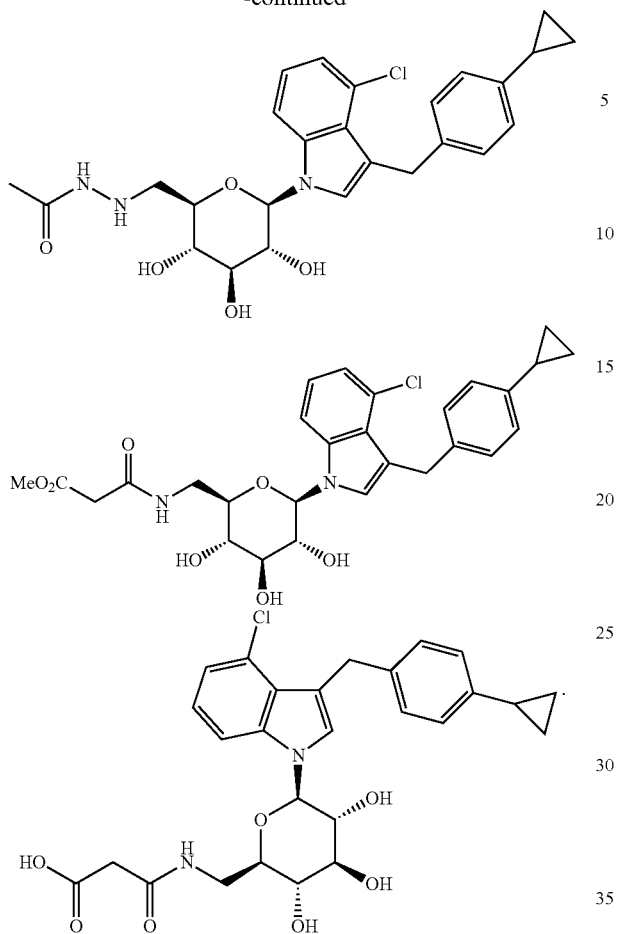

8. A compound of formula (III):

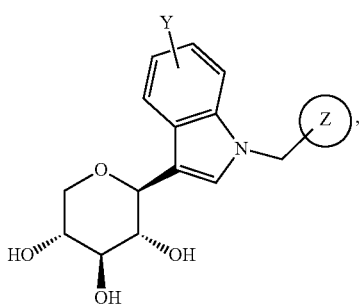

wherein

Y is H, halo, amino, $C_1$-$C_{10}$ alkyl, or $C_1$-$C_{10}$ alkoxyl; and

Z is unsubstituted aryl or aryl substituted with halo, hydroxyl, amino, $C_1$-$C_{10}$ alkyl, $C_1$-$C_{10}$ alkoxyl, $C_3$-$C_{10}$ cycloalkyl, $C_3$-$C_{10}$ heterocycloalkyl, $C_2$-$C_{10}$ alkenyl, $C_2$-$C_{10}$ alkynyl, aryl, or heteroaryl.

9. The compound of claim 8, wherein Y is H or halo, and Z is unsubstituted aryl or aryl substituted with $C_3$-$C_{10}$ cycloalkyl.

10. The compound of claim 8, wherein is the compound is one of the compounds as shown below:

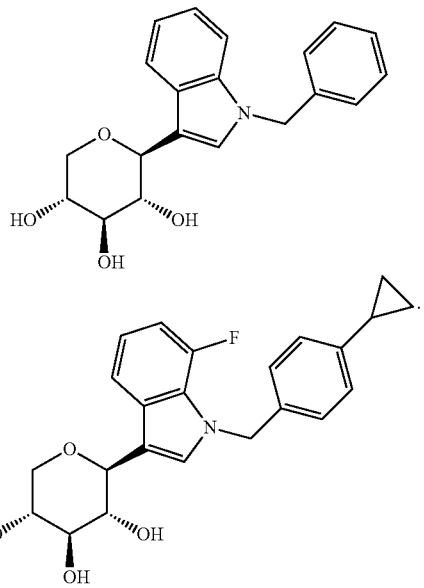

11. A pharmaceutical composition comprising a pharmaceutically acceptable carrier and a compound of claim 1.

12. A method of treating a disorder related to sodium-dependent glucose co-transporter 2, comprising administering to a subject in need thereof an effective amount of a compound of claim 1, wherein the disorder is type 1 diabetes mellitus, type 2 diabetes mellitus, or hyperglycemia.

13. The method of claim 12, further comprising administering to the subject an antidiabetic agent, an anti-obesity agent, an anti-diabetic complications agent, an antihypertensive agent, an antiplatelet agent, an anti-atherosclerotic agent, or a hypolipidemic agent.

14. A pharmaceutical composition comprising a pharmaceutically acceptable carrier and a compound of claim 5.

15. A method of treating a disorder related to sodium-dependent glucose co-transporter 2, comprising administering to a subject in need thereof an effective amount of a compound of claim 5, wherein the disorder is type 1 diabetes mellitus, type 2 diabetes mellitus, or hyperglycemia.

16. The method of claim 15, further comprising administering to the subject an antidiabetic agent, an anti-obesity agent, an anti-diabetic complications agent, an antihypertensive agent, an antiplatelet agent, an anti-atherosclerotic agent, or a hypolipidemic agent.

17. A pharmaceutical composition comprising a pharmaceutically acceptable carrier and a compound of claim 8.

18. A method of treating a disorder related to sodium-dependent glucose co-transporter 2, comprisingadministering to a subject in need thereof an effective amount of a compound of claim 8, wherein the disorder is type 1 diabetes mellitus, type 2 diabetes mellitus, or hyperglycemia.

19. The method of claim 18, further comprising administering to the subject an antidiabetic agent, an anti-obesity agent, an anti-diabetic complications agent, an antihypertensive agent, an antiplatelet agent, an anti-atherosclerotic agent, or a hypolipidemic agent.

* * * * *